United States Patent
Clegg et al.

(10) Patent No.: US 8,828,384 B2
(45) Date of Patent: Sep. 9, 2014

(54) COMPOUNDS

(71) Applicant: GlaxoSmithKline, Philadelphia, PA (US)

(72) Inventors: Stephanie Jane Clegg, Stevenage (GB); Eric Dobrzynski, King of Prussia, PA (US); Jonathan H. Ellis, Stevenage (GB); Volker Germaschewski, Stevenage (GB); Alexis Pual Godillot, King of Prussia, PA (US); Zdenka Ludmila Jonak, King of Prussia, PA (US); Alan P. Lewis, Stevenage (GB); John R. White, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/927,352

(22) Filed: Jun. 26, 2013

(65) Prior Publication Data
US 2014/0010807 A1    Jan. 9, 2014

Related U.S. Application Data

(62) Division of application No. 12/596,262, filed as application No. PCT/US2008/006424 on Apr. 16, 2008, now Pat. No. 8,496,932.

(60) Provisional application No. 61/044,132, filed on Apr. 11, 2008.

(51) Int. Cl.
*A61K 39/395* (2006.01)

(52) U.S. Cl.
USPC .................................. 424/130.1; 530/387.1

(58) Field of Classification Search
None
See application file for complete search history.

(56) References Cited

U.S. PATENT DOCUMENTS 8,454,960 B2 *  6/2013  Barbas, III ................. 424/134.1

\* cited by examiner

*Primary Examiner* — Laura B Goddard
*Assistant Examiner* — Meera Natarajan
(74) *Attorney, Agent, or Firm* — William T. Han; Jonathan M. Dermott

(57) ABSTRACT

The present invention relates to an antibody which has multiple specificities. In particular the antibody of the present invention binds to (cross react with) human IL-8, Gro-alpha, Gro-beta, Gro-gamma, and ENA-78.

4 Claims, 7 Drawing Sheets

Figure 2

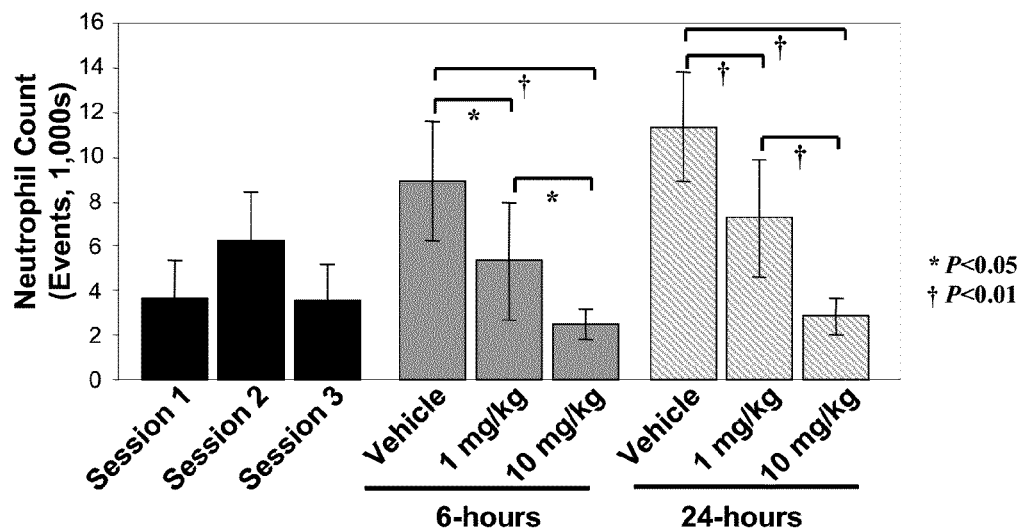

Flow cytometric data comparing neutrophils present in BAL samples. Sessions 1, 2 and 3 are presented. The black solid bars show the baselines 5 day pre-LPS challenge. The grey solid bars depict the BAL data 6-hours post LPS challenge. The Chimera Antibody treatment significantly and dose dependently inhibited neutrophil infiltration. The grey hatched bars represent 24-hour data. (n=6, *$p \leq 0.05$, †$p \leq 0.01$, error bars represent standard deviation).

Figure 3

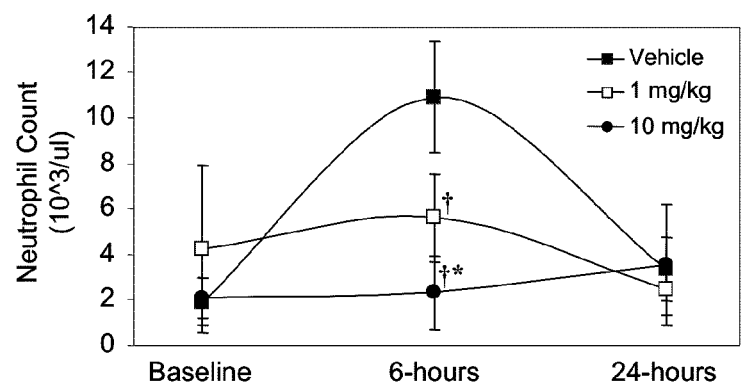

Hematological analysis of total circulating neutrophils (cell count). IV injection of 1 (open squares, □) and 10 mg/kg (closed circles, •) of the Chimera Antibody prevented inhaled LPS stimulation of circulating neutrophils. Both 1 and 10 mg/kg treatments are significantly reduced compared to the vehicle NHP (†) and 10 mg/kg treatment was also significantly reduced compared to the 1 mg/kg dose (*). Data are represented as total count per ul of blood (n=6, *$p \leq 0.05$ vs. 1 mg/kg, †$p \leq 0.01$ vs. vehicle, error bars represent standard deviation).

Figure 4

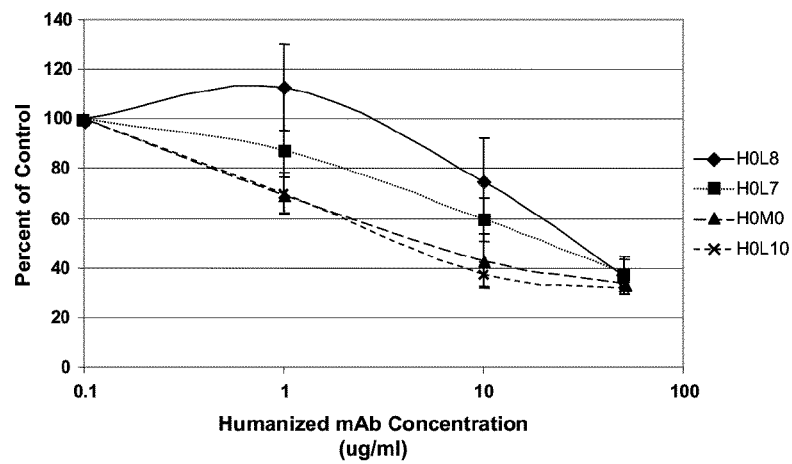

Inhibition human IL-8 stimulated neutrophil activation (increased CD11b surface expression). Various concentrations of the humanized penta-specific antibodies were pre-incubated with 10 nM hIL-8 prior to addition to purified human neutrophils. Data are expressed as mean values of 4 different donors (n=4). Bars represent standard error. All samples are compared to purified neutrophils stimulated with hIL-8 only (no mAb prior to addition to purified neutrophils). Humanized construct H0L10 and H0M0 are more effective at inhibiting hIL-8 stimulated CD11b surface expression.

Mouse 2X656.35 mAb binding to target human chemokines.

The Chimera Antibody (HcLc) mAb binding to human target chemokines.

hIL-18 run as a negative control

Humanized mAbs binding to human target chemokines hIL-18 run as a negative control

COMPOUNDS

CROSS-REFERENCE TO RELATED APPLICATION

This application is a divisional application of U.S. application Ser. No. 12/596,262, filed Oct. 16, 2009 which is a 371 of International Application No. PCT/US2008/06424, filed Apr. 16, 2008, which claims the benefit of U.S. Provisional Application No. 61/044,132 filed, Apr. 11, 2008 and 60/912,229, filed, Apr. 17, 2007 which are incorporated herein in their entirety.

FIELD OF THE INVENTION

The present invention relates to an antibody which has multiple specificities. In particular the antibody of the present invention binds to (cross react with) human IL-8, Gro-alpha, Gro-beta, Gro-gamma, and ENA-78. The present invention also concerns with methods of treating diseases or disorders characterised by elevated or unbalanced level of one or more of human IL-8, Gro-alpha, Gro-beta, Gro-gamma, and ENA-78, particularly COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis with said antibody.

BACKGROUND OF THE INVENTION

Published data and reports indicate that the members of the ELRCXC subfamily of CXCL chemokines are elevated in a number of diseases. There are a total of 16 CXCL family members. The chemokines are reported to be up-regulated in a number of inflammatory diseases, including COPD, in which CXCL1-3, 5, and 8, also known as Gro-α, -β, -γ (Haskill, S., et al. Proc. Natl. Acad. Sci., 1990: 87, 7732-7736), ENA-78 (Wang, D. and Richmond, A., Cytokine Reference. Oppenheim, J. J. and Feldman, M. ed., Academic Press, London, 1023-1027, Powerm C. A. et al. Gene., 1994: 151, 333-334), and IL-8 (Iizasa, H. and Matsushima, K., Cytokine Reference. Oppenheim, J. J. and Feldman, M. ed., Academic Press, London, 1061-1067, Matsushima, K. et al., J. Exp. Med. 1988: 167, 1883-1893) respectively (Am. J. Respir. Crit Care Med., 163: 349-355, 2001, Am. J. Respir. Crit Care Med., 168: 968-975, 2003, Thorax, 57: 590-595, 2002). It has be postulated that prolonged and elevated expression of these chemokines could be involved in the development of diseases such as COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, or endometriosis. These CXC chemokines are known to stimulate neutrophil chemotaxis by engaging and activating the CXCR1 and/or CXCR2 receptors. Thus the inhibition of these chemokines could prevent inflammatory cells from infiltrating the lung tissue and thus prevent tissue damage. The present invention is directed to inhibiting the activation of CXCR1 and CXCR2 receptors by using an antibody having the ability to bind to human IL-8, Gro-alpha, Gro-beta, Gro-gamma, and ENA-78, i.e. a penta-specific antibody.

SUMMARY OF THE INVENTION

The present invention relates to an antibody (immunoglobulin) which has multiple specificities contained within one immunoglobulin. In particular the antibody of the present invention binds to (cross react with) human IL-8, Gro-alpha, Gro-beta, Gro-gamma, and ENA-78. The present invention also concerns with methods of treating diseases or disorders characterised by elevated or unbalanced level of one or more of human IL-8, Gro-alpha, Gro-beta, Gro-gamma, and ENA-78, particularly COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis with said antibody.

In one aspect, the present invention relates to an isolated antibody which has multiple specificity to (or cross reacts with) human IL-8, Gro-alpha, Gro-beta, Gro-gamma, and ENA-78; thus we define the antibody of the present invention as penta-specific (or pan-ELR) antibody. The definition of antibody includes an antigen binding portion (or fragment) of the antibody such that the antigen binding portion (or fragment) binds to human IL-8, Gro-alpha, Gro-beta, Gro-gamma, and ENA-78. The penta-specific antibody of the invention is preferably murine monoclonal, chimeric, human or humanized. For avoidance of doubt, the penta-specific antibody of the present invention need not bind solely to human IL-8, Gro-alpha, Gro-beta, Gro-gamma, and ENA-78 antigens, but it may also to bind to other related proteins (such as human GCP-2, or may even bind to non-human orthologues of IL-8, Gro-alpha, Gro-beta, Gro-gamma, ENA-78, and GCP-2); in other words, the penta-specific antibody of the present invention minimally binds to human IL-8, Gro-alpha, Gro-beta, Gro-gamma, and ENA-78.

Preferably, a penta-specific antibody of the present invention binds to each of human IL-8, Gro-alpha, Gro-beta, Gro-gamma, and ENA-78 with equilibrium constant, KD, values of less than $10^{-7}$ M, more preferably less than $10^{-8}$ M, and even more preferably less than $10^{-9}$ M as determined by surface plasmon resonance. Typically surface plasmon resonance measurement is conducted as described below.

In one embodiment the present invention comprises a method of decreasing the neutrophil chemotaxis through inhibition of CXCR1 and CXCR2 receptor activation by neutralizing human IL-8, Gro-alpha, Gro-beta, Gro-gamma, GCP-2 and ENA-78 with a penta-specific antibody of the present invention.

In one embodiment the present invention relates to a method of decreasing the neutrophil chemotaxis in a patient in need thereof by administering a penta-specific antibody of the present invention.

In one embodiment, a penta-specific antibody binds within epitope of KELRCQCIKTYSKP (SEQ ID NO: 54) in human IL-8.

In one embodiment, the penta-specific antibody of the present invention is generated by a method comprising the steps of using RIMMs (Kilpatrick, K. E., et al. Hybridoma. 1997: 16, 381.) type protocol using a mixture (cocktail) of human IL-8, Gro-alpha, Gro-beta, Gro-gamma, and ENA-78 together with a set of five multiple antigenic peptides (MAPs) each MAP unit having one separate sequence from polypeptides of ID NOs: 49-53.

```
LATELRSQSLQTLQG    SEQ ID NO: 49

SAKELRSQSIKTYSK    SEQ ID NO: 50

LRELRSVSLQTTQG     SEQ ID NO: 51

SPGPHSAQTEVIAT     SEQ ID NO: 52

ESGPHSANTEIIVK     SEQ ID NO: 53
```

Without being bound by theory, MAPs serve two functions within the immunization protocol. First, MAPs allow for a selective multiple presentation of a known target amino acid sequence to the host immune system. Secondly, the increase in mass, due to multiple copies of the sequence linked via a core, such as, but not limited to lysine, increases the immunogenicity of the sequence over that of individual peptides (Francis, J. P., et al., Immunology, 1991: 73; 249, Schott, M. E., et al., Cell. Immuno. 1996: 174: 199-209, Tam, J. P. Proc. Natl. Acad. Sci. 1988: 85; 5409-5413).

The MAPs used to generate this invention are comprised of multiple copies of the conserved target sequences (e.g. SEQ ID NOs: 49-53) found with and around the ELRCXC and GPHCA regions of target chemokines Exemplary MAP set is depicted in FIG. 1.

In one embodiment, a penta-specific antibody of the present invention is generated by a method comprising the steps of:
 a. injecting into a mouse a mixture of human IL-8, Gro-alpha, Gro-beta, Gro-gamma, and ENA-78 in complete Freund's adjuvant (cFA);
 b. injecting into the mouse a mixture of human IL-8, Gro-alpha, Gro-beta, Gro-gamma, and ENA-78 in incomplete Freund's adjuvant (iFA); and
 c. injecting into the mouse a mixture of human IL-8, Gro-alpha, Gro-beta, Gro-gamma, and ENA-78, and a set of five multiple antigenic peptides (MAPs), each MAP unit having one separate sequence from polypeptides of ID NOs: 49-53 in incomplete Freund's adjuvant;
 d. isolating B cells from the mouse;
 e. fusing the B cells with myeloma cells to form immortal hybridoma cells that secrete the desired penta-specific antibody; and
 f. isolating the penta-specific antibody from the culture supernatant of the hybridoma.

If desired, one can optionally inject into the mouse a mixture of human IL-8, Gro-alpha, Gro-beta, Gro-gamma, and ENA-78, and a set of MAPs comprising amino acid sequences of SEQ ID NOs: 49-53 in PBS between steps c and d.

In another embodiment, a penta-specific antibody of the present invention is generated by a method comprising the steps of:
 a. injecting into a mouse a set of five multiple antigenic peptides (MAPs) each MAP unit having one separate sequence from polypeptides of ID NOs: 49-53 (hereinafter also referred to as the MAP set) in complete Freund's adjuvant;
 b. injecting into the mouse the MAP set in incomplete Freund adjuvant;
 c. injecting into the mouse a mixture of all human IL-8, Gro-alpha, Gro-beta, Gro-gamma, and ENA-78, and the MAP set in incomplete Freund's adjuvant;
 d. isolating B cells from the mouse; and
 e. fusing the B cells with myeloma cells to form immortal hybridoma cells that secrete the desired penta-specific antibody; and
 f. isolating the penta-specific antibody from the culture supernatant of the hybridoma.

If desired, one can optionally inject into the mouse a mixture of human IL-8, Gro-alpha, Gro-beta, Gro-gamma, and ENA-78, and a set of MAPs having SEQ ID NOs: 49-53 in PBS between steps c and d.

In another embodiment, the present invention concerns a penta-specific antibody made by the foregoing process.

In one embodiment, a penta-specific antibody has heavy and light chain variable regions encoded by nucleotide sequences comprising sequences of SEQ ID NO:1 and SEQ ID NO:3, respectively, or conservative sequence modifications thereof.

In one embodiment, a penta-specific antibody has heavy and light chain variable regions encoded by nucleotide sequences comprising sequences of SEQ ID NO:5 and SEQ ID NO:7, respectively, or conservative sequence modifications thereof.

In one embodiment, a penta-specific antibody has heavy chain variable region encoded by a nucleotide sequence comprising sequence of SEQ ID NO:9, or conservative sequence modifications thereof.

In one embodiment, a penta-specific antibody has heavy and light chain variable regions comprising the amino acid sequences of SEQ ID NO:2 and SEQ ID NO:4, respectively, or conservative sequence modifications thereof.

In one embodiment, a penta-specific antibody has heavy and light chain variable regions comprising polypeptides which are at least 90%, 95%, 98% or 99% identical to the amino acid sequences of SEQ ID NO:2 and SEQ ID NO:4, respectively.

In one embodiment, a penta-specific antibody has heavy and light chain variable regions comprising the amino acid sequences of SEQ ID NO:6 and SEQ ID NO:8, respectively, or conservative sequence modifications thereof.

In one embodiment, a penta-specific antibody has heavy and light chain variable regions comprising polypeptides which are at least 90%, 95%, 98% or 99% identical to the amino acid sequences of SEQ ID NO:6 and SEQ ID NO:8, respectively.

In one embodiment, a penta-specific antibody has heavy and light variable regions comprising the amino acid sequences of SEQ ID NOs:10 and 12, respectively, or conservative sequence modifications thereof.

In one embodiment, a penta-specific antibody has heavy and light chain variable regions comprising polypeptide sequences which are at least 90%, 95%, 98% or 99% identical to the amino acid sequences of SEQ ID NOs:10 and 12, respectively.

In one embodiment, a penta-specific antibody comprises at least one variable region selected from (i) the amino acid SEQ ID NO: 2, 4, 6, 8, 10, or 12; or (ii) an amino acid sequence which is at least 90%, 95%, 98% or 99% identical to any one of the amino acid sequences of (i) above.

In one embodiment, a penta-specific antibody comprises CDR sequences of SEQ ID NOs: 13, 14, 15, 16, 17, and 18; or one or more of the CDR sequences can be conservative sequence modifications of the sequences SEQ ID NOs: 13, 14, 15, 16, 17, and 18.

In one embodiment, the present invention relates to hybridoma or transfectoma which produces a penta-specific antibody which comprises CDR sequences of SEQ ID NOs: 13, 14, 15, 16, 17, and 18.

In one embodiment, the present invention relates to a recombinant eukaryotic or prokaryotic cell which produces a penta-specific antibody which comprises CDR sequences of SEQ ID NOs: 13, 14, 15, 16, 17, and 18.

In one embodiment, a penta-specific antibody comprises at least one CDR sequence selected from (i) SEQ ID NO: 13, 14, 15, 16, 17, or 18; or (ii) a conservative sequence modification of the sequences listed in (i).

In one embodiment, a penta-specific antibody comprises a polypeptide of SEQ ID NO:15.

In one embodiment, a penta-specific antibody comprises at least four CDR sequences selected from the group consisting of SEQ ID NOs: 13, 14, 15, 16, 17, and 18; or one or more of the CDR sequences can be conservative sequence modifications of the sequences listed in SEQ ID NOs: 13, 14, 15, 16, 17, and 18.

In one embodiment, a penta-specific antibody comprises heavy and light chain variable regions which comprise the CDR amino acid sequences of SEQ ID NOs: 13, 14, and 15, and SEQ ID NOs: 16, 17, and 18, respectively.

In one embodiment, a penta-specific antibody comprises CDR sequences of SEQ ID NOs: 19, 20, 21, 22, 23, and 24; or one or more the CDR sequences can be conservative sequence modifications of the sequences listed in SEQ ID NOs: 19, 20, 21, 22, 23, and 24.

In one embodiment, the present invention relates to an hybridoma or transfectoma which produces a penta-specific antibody which comprises CDR sequences of SEQ ID NOs: 19, 20, 21, 22, 23, and 24.

In one embodiment, the present invention relates to a recombinant eukaryotic or a prokaryotic cell which produces a penta-specific antibody which comprises CDR sequences of SEQ ID NOs: 19, 20, 21, 22, 23, and 24.

In one embodiment, a penta-specific antibody comprises at least one CDR sequence selected from (i) SEQ ID NO: 19, 20, 21, 22, 23, or 24; or (ii) a conservative sequence modification of the sequences listed in (i).

In one embodiment, a penta-specific antibody comprises a polypeptide of SEQ ID NO:21.

In one embodiment, a penta-specific antibody comprises at least four CDR sequences selected from the group consisting of: SEQ ID NOs: 19, 20, 21, 22, 23, and 24; or one or more of the CDR sequences can be conservative sequence modifications of the sequences listed in SEQ ID NOs: 19, 20, 21, 22, 23, and 24.

In one embodiment, a penta-specific antibody comprises heavy and light chain variable regions which comprise the CDR amino acid sequences of SEQ ID NOs: 19, 20, and 21, and SEQ ID NOs: 22, 23, and 24, respectively.

In one embodiment, a penta-specific antibody comprises CDR sequences of SEQ ID NOs: 25, 26, 27, 28, 29, and 30; or one or more the CDR sequences can be conservative sequence modifications of the sequences listed in SEQ ID NOs: 25, 26, 27, 28, 29, and 30.

In one embodiment, the present invention relates to an hybridoma or transfectoma which produces a penta-specific antibody which comprises CDR sequences of SEQ ID NOs: 25, 26, 27, 28, 29, and 30.

In one embodiment, the present invention relates to a recombinant eukaryotic or prokaryotic cell which produces a penta-specific antibody which comprises CDR sequences of SEQ ID NOs: 25, 26, 27, 28, 29 and 30.

In one embodiment, a penta-specific antibody comprises at least one CDR sequence selected from (i) SEQ ID NO: 25, 26, 27, 28, 29, or 30; or (ii) a conservative sequence modification of the sequences listed in (i).

In one embodiment, a penta-specific antibody comprises a polypeptide of SEQ ID NO:27.

In one embodiment, a penta-specific antibody comprises at least four CDR sequences selected from the group consisting of: SEQ ID NOs: 25, 26, 27, 28, 29, and 30; or one or more of the CDR sequences can be conservative modifications of the sequences listed in SEQ ID NOs: 25, 26, 27, 28, 29, and 30.

In one embodiment, a penta-specific antibody comprises heavy and light variable chain regions which comprise the CDR amino acid sequences of SEQ ID NOs: 25, 26, and 27, and SEQ ID NOs: 28, 29 and 30, respectively.

In one embodiment, the present invention concerns a hybridoma which produces a monoclonal antibody having heavy or light chain variable region encoded by nucleotide sequences comprising nucleotide sequences of SEQ ID NO:1, 5, or 9, or SEQ ID NO:3 or 7, respectively.

In one embodiment, the present invention concerns a hybridoma which produces a monoclonal antibody having heavy or light chain variable region comprising the amino acid sequences of SEQ ID NO:2, 6, or 10, or SEQ ID NO: 4, 8, or 12, respectively, and conservative sequence modifications thereof.

In one embodiment, the present invention relates to a recombinant eukaryotic or a prokaryotic host cell which produces a penta-specific antibody having heavy or light variable region which comprise the amino acid sequences of SEQ ID NO:2, 6, or 10, or SEQ ID NO:4, 8, or 12, respectively, and conservative sequence modifications thereof.

In one embodiment, the present invention relates to an expression vector comprising nucleotide sequences encoding a variable heavy or light chain of a penta-specific antibody comprising the CDR sequences of SEQ ID NOs: 13, 14, and 15; or SEQ ID NOs: 16, 17, and 18, respectively.

In one embodiment, the present invention relates to an expression vector comprising a nucleotide sequence encoding a CDR sequence of a penta-specific antibody selected from SEQ ID NO: 13, 14, 15, 16, 17, or 18.

In one embodiment, the present invention relates to an expression vector comprising nucleotide sequences encoding at least four CDR sequences of a penta-specific antibody selected from the group consisting of SEQ ID NOs: 13, 14, 15, 16, 17, and 18.

In one embodiment, the present invention relates to an expression vector comprising polynucleotide sequences of SEQ ID NOs: 31, 32, or 33.

In one embodiment, the present invention relates to an expression vector comprising polynucleotide sequences of SEQ ID NOs: 34, 35, and 36.

In one embodiment the present invention relates to an expression vector comprising at least four polynucleotide sequences selected from the group of SEQ ID NOs: 31, 32, 33, 34, 35, and 36.

In one embodiment, the present invention relates to an expression vector comprising nucleotide sequences encoding a variable heavy or light chain of a penta-specific antibody comprising the CDR sequences of SEQ ID NOs: 19, 20, and 21; or 22, 23, and 24, respectively.

In one embodiment, the present invention relates to an expression vector comprising a nucleotide sequence encoding a CDR sequence of a penta-specific antibody selected from SEQ ID NO: 19, 20, 21, 22, 23, or 24.

In one embodiment, the present invention relates to an expression vector comprising nucleotide sequences encoding at least four CDR sequences of a penta-specific antibody selected from the group consisting of SEQ ID NOs: 19, 20, 21, 22, 23, and 24.

In one embodiment, the present invention relates to an expression vector comprising polynucleotide sequences of SEQ ID NOs: 37, 38, and 39.

In one embodiment, the present invention relates to an expression vector comprising polynucleotide sequences of SEQ ID NOs: 40, 41, and 42.

In one embodiment the present invention relates to an expression vector comprising at least four polynucleotide sequences selected from the group of SEQ ID NOs: 37, 38, 39, 40, 41, and 42.

In one embodiment, the present invention relates to an expression vector comprising nucleotide sequences encoding a variable heavy chain of a penta-specific antibody comprising the CDR sequences of SEQ ID NOs: 25, 26, and 27.

In one embodiment, the present invention relates to an expression vector comprising a nucleotide sequence encoding a CDR sequence of a penta-specific antibody selected from SEQ ID NO: 25, 26, or 27.

In one embodiment, the present invention relates to an expression vector comprising polynucleotide sequences of SEQ ID NOs: 43, 44, and 45.

In one embodiment, a penta-specific antibody has heavy and light chains encoded by nucleotide sequences comprising sequences of SEQ ID NO:11, and SEQ ID NO:47, 59, 61, or 63, respectively.

In one embodiment, a penta-specific antibody has heavy and light chains encoded by nucleotide sequences comprising sequences which are at least 90%, 95%, 98% or 99% identical to sequences of SEQ ID NO:11, and SEQ ID NO:47, 59, 61, or 63, respectively.

In one embodiment, a penta-specific antibody has heavy and light chains comprising the amino acid sequences of SEQ ID NO:46, and SEQ ID NO:48, 60, 62, or 64, respectively.

In one embodiment, a penta-specific antibody has heavy and light chains comprising the amino acid sequences of SEQ ID NO:46 and SEQ ID NO:48, respectively.

In one embodiment, a penta-specific antibody has heavy and light chains comprising the amino acid sequences of SEQ ID NO:46 and SEQ ID NO:60, respectively.

In one embodiment, a penta-specific antibody has heavy and light chains comprising the amino acid sequences of SEQ ID NO:46 and SEQ ID NO: 62, respectively.

In one embodiment, a penta-specific antibody has heavy and light chains comprising the amino acid sequences of SEQ ID NO:46 and SEQ ID NO:64, respectively.

In one embodiment, a penta-specific antibody has heavy and light chains comprising polypeptides which are at least 90%, 95%, 98% or 99% identical to the amino acid sequences of SEQ ID NO:46, and SEQ ID NO:48, 60, 62, or 64, respectively.

In one embodiment, the present invention relates to a recombinant eukaryotic or a prokaryotic host cell which produces a penta-specific antibody having heavy or light chain comprising the amino acid sequence of SEQ ID NO: 46, or SEQ ID NO:48, 60, 62, or 64, respectively.

In one embodiment, the present invention relates to a recombinant eukaryotic or a prokaryotic host cell which produces a penta-specific antibody having heavy and light chains comprising the amino acid sequences of SEQ ID NO: 46, and SEQ ID NO:48, 60, 62, or 64, respectively.

In one embodiment, the present invention relates to a recombinant eukaryotic or a prokaryotic host cell which produces a penta-specific antibody having heavy or light chain comprising the amino acid sequence which is at least 90%, 95%, 98% or 99% identical to the amino acid sequence of SEQ ID NO: 46, or SEQ ID NO:48, 60, 62, or 64, respectively.

In one embodiment, the present invention relates to a recombinant eukaryotic or a prokaryotic host cell which produces a penta-specific antibody having heavy and light chains comprising the amino acid sequences which are at least 90%, 95%, 98% or 99% identical to the amino acid sequences of SEQ ID NO: 46, and SEQ ID NO:48, 60, 62, or 64, respectively.

In one embodiment, the present invention relates to an expression vector comprising polynucleotide sequences comprising sequences of SEQ ID NO:11, and SEQ ID NO:47, 59, 61, or 63, respectively.

In one embodiment, the present invention relates to an expression vector comprising polynucleotide sequences comprising sequences which are at least 90%, 95%, 98% or 99% identical to sequences of SEQ ID NO:11, and SEQ ID NO:47, 59, 61, or 63, respectively.

In one embodiment, the present invention relates to an expression vector comprising a polynucleotide sequence comprising a sequence of SEQ ID NO:11, 47, 59, 61, or 63.

In one embodiment, the present invention relates to an expression vector comprising a polynucleotide sequence comprising a sequence which is at least 90%, 95%, 98% or 99% identical to a sequence of SEQ ID NO:11, 47, 59, 61, or 63, respectively.

In one embodiment, the present invention relates to an expression vector comprising polynucleotide sequences which encode a penta-specific antibody comprising heavy and light chains comprising the amino acid sequences of SEQ ID NO:46, and SEQ ID NO:48, 60, 62, or 64, respectively.

In one embodiment, the present invention relates to an expression vector comprising polynucleotide sequences which encode a penta-specific antibody comprising heavy and light chains comprising the amino acid sequences which are at least 90%, 95%, 98% or 99% identical to the amino acid sequences of SEQ ID NO:46, and SEQ ID NO:48, 60, 62, or 64, respectively.

In one embodiment, the present invention relates to an expression vector comprising a polynucleotide sequence which encode a polypeptide comprising the amino acid sequence of SEQ ID NO:46, 48, 60, 62, or 64.

In one embodiment, the present invention relates to an expression vector comprising a polynucleotide sequence which encode a polypeptide comprising an amino acid sequence which is at least 90%, 95%, 98% or 99% identical to the amino acid sequences of SEQ ID NO:46, 48, 60, 62, or 64.

In one embodiment the present invention relates to a process for producing a penta-specific antibody (immunoglobulin) in a single host cell, comprising the steps of:
(i) transforming said single host cell with a first DNA sequence encoding a heavy chain comprising polypeptide of SEQ ID NO: 46; and a second DNA sequence encoding a light chain comprising a polypeptide of SEQ ID NO: 48, 60, 62, or 64; and
(ii) expressing said first DNA sequence and said second DNA sequence so that said immunoglobulin heavy and light chains are produced as separate molecules in said transformed single host cell;
furthermore, this process can be carried out such that said first and second DNA sequences are present in different vectors or said first and second DNA sequences are present in a single vector.

In one embodiment the present invention relates to a process for producing a penta-specific antibody (immunoglobulin) in a single host cell, comprising the steps of:
(i) transforming said single host cell with a first DNA sequence encoding at least the variable domain of the immunoglobulin heavy chain comprising CDR domains of SEQ ID NOs: 13, 14, and 15; and a second DNA sequence encoding at least the variable domain of the immunoglobulin light chain comprising CDR domains of SEQ ID NOs: 16, 17, and 18; and (ii) expressing said first DNA sequence and said second DNA sequence so that said immunoglobulin heavy and light chains are produced as separate molecules in said transformed single host cell;

furthermore, this process can be carried out such that said first and second DNA sequences are present in different vectors or said first and second DNA sequences are present in a single vector.

In one embodiment the present invention relates to a process for producing a penta-specific antibody (immunoglobulin) in a single host cell, comprising the steps of:

(i) transforming said single host cell with a first DNA sequence encoding at least the variable domain of the immunoglobulin heavy chain comprising CDR domains of SEQ ID NOs: 19, 20, and 21; and a second DNA sequence encoding at least the variable domain of the immunoglobulin light chain comprising CDR domains of SEQ ID NOs: 22, 23, and 24; and (ii) expressing said first DNA sequence and said second DNA sequence so that said immunoglobulin heavy and light chains are produced as separate molecules in said transformed single host cell;

this process can be carried out such that said first and second DNA sequences are present in different vectors or said first and second DNA sequences are present in a single vector.

In one embodiment the present invention relates to an antibody that fully or partially blocks the binding of any one of the aforementioned penta-specific antibody to human IL-8, Gro-alpha, Gro-beta, Gro-gamma, ENA-78, and GCP-2 in an immunoassay, such as ELISA assay. In one embodiment, partial blocking occurs when the antibody blocks the binding of the penta-specific antibody by more than 10%, 20%, 40% or 50%.

In one embodiment the present invention relates to an antibody that competes with the binding of any of the aforementioned penta-specific antibody to human IL-8, Gro-alpha, Gro-beta, Gro-gamma, ENA-78, and GCP-2.

In one embodiment the present invention relates to an antibody that fully or partially blocks the binding of any one of the aforementioned penta-specific antibody to epitope of KELRCQCIKTYSKP (SEQ ID NO: 54) in human IL-8 in an immunoassay, such as ELISA assay. In one embodiment, partial blocking occurs when the antibody blocks the binding of the penta-specific antibody by more than 10%, 20%, 40% or 50%.

In one embodiment the present invention relates to an antibody that competes with the binding of any one of the aforementioned penta-specific antibody to epitope of KELRCQCIKTYSKP (SEQ ID NO: 54) in human IL-8.

In one embodiment, the present invention relates to a composition comprising an aforementioned penta-specific antibody and a pharmaceutically acceptable carrier.

In one embodiment, the present invention relates to a method of treating or preventing in a mammal COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis comprising administering an effective amount of an aforementioned penta-specific antibody to said mammal.

In one embodiment the present invention relates to an aforementioned penta-specific antibody for use in the treatment of diseases or disorders characterised by elevated or unbalanced level of one or more of human IL-8, Gro-alpha, Gro-beta, Gro-gamma, GCP-2 and ENA-78, particularly COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, or endometriosis.

In one aspect, the present invention relates to an aforementioned penta-specific antibody for use in preventing and/or treating COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis in a mammal.

In one aspect, the present invention relates to use of an aforementioned penta-specific antibody in the manufacture of a medicament for use in preventing and/or treating COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis in a mammal.

In one aspect, the present invention relates to use of an aforementioned penta-specific antibody in the manufacture of a medicament for preventing and/or treating COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis in a mammal.

In one embodiment, above mammal is human.

DESCRIPTION OF FIGURES

FIG. 2 shows flow cytometric data comparing neutrophils present in BAL samples. Sessions 1, 2 and 3 are presented. The black solid bars show the baselines 5 day pre-LPS challenge. The grey solid bars depict the BAL data 6-hours post LPS challenge. The Chimera Antibody (HcLc) treatment significantly and dose dependently inhibited neutrophil infiltration. The grey hatched bars represent 24-hour data. (n=6, *p≤0.05, †p≤0.01, error bars represent standard deviation).

FIG. 3 shows hematological analysis of total circulating neutrophils (cell count). IV injection of 1 (open squares, □) and 10 mg/kg (closed circles, •) of the Chimera Antibody (HcLc) prevented inhaled LPS stimulation of circulating neutrophils. Both 1 and 10 mg/kg treatments are significantly reduced compared to the vehicle NHP (†) and 10 mg/kg treatment was also significantly reduced compared to the 1 mg/kg dose (*). Data are represented as total count per ul of blood (n=6, *p≤0.05 vs. 1 mg/kg, †p≤0.01 vs. vehicle, error bars represent standard deviation).

FIG. 4 shows inhibition human IL-8 stimulated neutrophil activation (increased CD11b surface expression). Various concentrations of the humanized penta-specific antibodies were pre-incubated with 10 nM hIL-8 prior to addition to purified human neutrophils. Data are expressed as mean values of 4 different donors (n=4). Bars represent standard error. All samples are compared to purified neutrophils stimulated with hIL-8 only (no mAb prior to addition to purified neutrophils). Humanized construct H0L10 and HOMO are more effective at inhibiting hIL-8 stimulated CD11b surface expression.

DETAILED DESCRIPTION OF THE INVENTION

Figure 1:
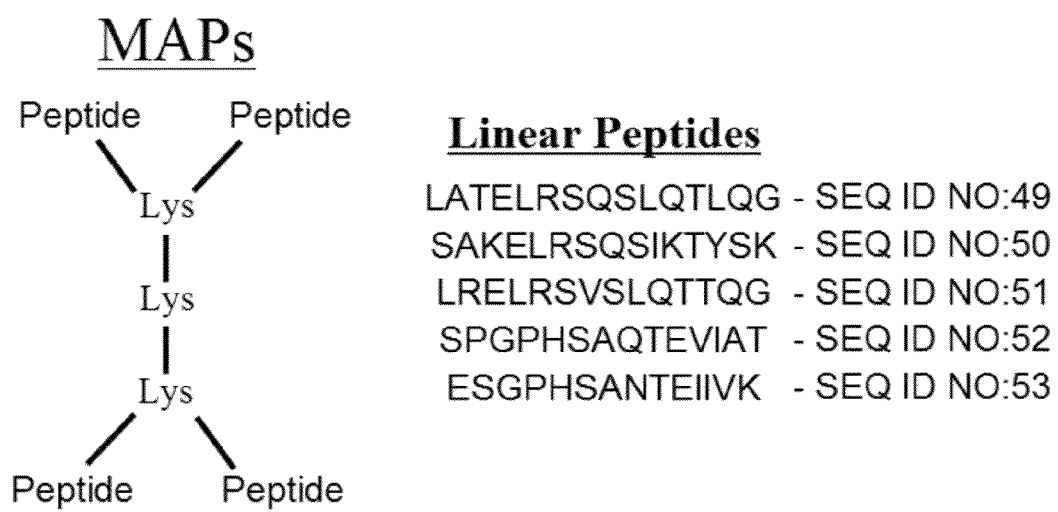
FIG. 1 depicts an exemplary set of MAPs to generate a penta-specific antibody. For avoidance of doubt, five MAP peptide units are depicted. Each unit contains one identical amino acid sequence selected from linear peptides of SEQ ID NO: 49-53.

An "isolated penta-specific antibody" or simply "penta-specific antibody", as used herein, is intended to refer to an antibody that binds to and therefore cross reacts with human IL-8, Gro-alpha, Gro-beta, Gro-gamma, and ENA-78, and is substantially free of other antibodies having different antigenic specificities, and furthermore, is a single composition of matter. For avoidance of doubt, the penta-specific antibody of the present invention need not bind solely to human IL-8, Gro-alpha, Gro-beta, Gro-gamma, and ENA-78 antigens, but it may also happen to bind to other related proteins, such as human GCP-2, or may even bind to non-human orthologues of IL-8, Gro-alpha, Gro-beta, Gro-gamma, ENA-78, and GCP-2; in other words the penta-specific antibody of the present invention minimally binds to human IL-8, Gro-alpha, Gro-beta, Gro-gamma, and ENA-78. Moreover, an isolated penta-specific antibody is substantially free of other cellular material and/or chemicals. A penta-specific antibody, as used in this context, also includes antigen binding fragments and/or derivatives having the binding characteristics of their "parent" penta-specific antibody. The penta-specific antibody of the present invention may comprise two identical heavy chains and two identical light chains, forming the typical, bilaterally symmetric immunoglobulin molecule comprised of two heterodimers which are each comprised of a heavy chain and a light chain. Accordingly, the penta-specific antibody of the present invention may comprise two copies of the same antigen binding domain formed by the association of one heavy chain with one light chain. The penta-specific antibody of the present invention, though having only one kind of binding domain is still able to bind to and therefore cross react with human IL-8, Gro-alpha, Gro-beta, Gro-gamma, and ENA-78.

As used herein, "antibody" is also referred to as "immunoglobulin".

As used herein, "an antibody that cross reacts with" means the antibody binds not only to one antigen but binds to other antigens as well.

"Neutralizing," as used herein is intended to refer to a partial or full inhibition of at least one biological activities of human IL-8, Gro-alpha, Gro-beta, Gro-gamma, GCP-2, or ENA-78. For example, one of the biological activities of human IL-8, Gro-alpha, Gro-beta, Gro-gamma, GCP-2, or ENA-78 is its ability to induce neutrophil chemotaxis.

One way of measuring the binding kinetics of an antibody is by surface plasmon resonance. The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics.

A "monoclonal antibody" or mAb (as opposed to polyclonal antibody) as used herein is intended to refer to a preparation of antibody molecules of single molecular composition. For example, a murine derived monoclonal antibody (mouse monoclonal antibody) can be prepared by hybridoma technology, such as the standard Kohler and Milstein hybridoma methodology.

Antibody-producing cells can be obtained from the subject and used to prepare monoclonal antibodies by standard techniques, such as the hybridoma technique originally described by Kohler and Milstein (1975, Nature 256:495-497) (see also, Brown et al. (1981) J. Immunol 127:539-46; Brown et al. (1980) J Biol Chem 255:4980-83; Yeh et al. (1976) PNAS 76:2927-31; and Yeh et al. (1982) Int. J. Cancer 29:269-75). The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet., 3:231-36).

The term "transfectoma", as used herein, includes recombinant eukaryotic host cell expressing the antibody, such as CHO cells, NS/0 cells, HEK293 cells, plant cells, or fungi, including yeast cells.

As used herein, "specific" binding refers to antibody binding to a predetermined antigen. Typically, the antibody binds with an equilibrium constant, KD, corresponding to about $1 \times 10^{-7}$ M or less, and binds to the predetermined antigen with an affinity corresponding to a KD that is at least two orders of magnitude lower than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "kd" (sec-1), as used herein, is intended to refer to the dissociation rate constant of a particular antibody-antigen interaction.

The term "ka" (M×sec-1), as used herein, is intended to refer to the association rate constant of a particular antibody-antigen interaction.

The term "KD" (M), as used herein, is intended to refer to the equilibrium constant of a particular antibody-antigen interaction and is obtained by dividing the kd by the ka.

"Conservative sequence modifications" for nucleotide and amino acid sequence modifications means changes which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequences by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an antibody for which sequence is specifically disclosed is preferably replaced with another amino acid residue from the same side chain family. Thus in one aspect, the penta-specific antibody of the present invention includes all the conservative sequence modifications of the specifically disclosed amino acid sequences.

The present invention also encompasses "derivatives" of the amino acid sequences as specifically disclosed, wherein one or more of the amino acid residues have been derivatized, e.g., by acylation or glycosylation, without significantly affecting or altering the binding characteristics of the antibody containing the amino acid sequences.

For nucleic acids, the term "substantial identity" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial identity when the segments will hybridize under selective hybridization conditions, to the complement of the strand.

For nucleotide and amino acid sequences, the term "identity" indicates the degree of identity between two nucleic acid or amino acid sequences when optimally aligned and compared with appropriate insertions or deletions. Alternatively, substantial identity exists when the DNA segments will hybridize under selective hybridization conditions, to the complement of the strand.

The percent identity between two sequences is a function of the number of identical positions shared by the sequences (i.e., % identity=# of identical positions/total # of positions times 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide or polypeptide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

A nucleic acid is "operably linked" when it is placed into a functional relationship with another nucleic acid sequence. For instance, a promoter or enhancer is operably linked to a coding sequence if it affects the transcription of the sequence. With respect to transcription of regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

1. Antibody Structures

Intact Antibodies

Intact antibodies are usually heteromultimeric glycoproteins comprising at least two heavy and two light chains. Aside from IgM, intact antibodies are heterotetrameric glycoproteins of approximately 150 Kda, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain ($V_H$) followed by a number of constant regions. Each light chain has a variable domain ($V_L$) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade. The human IgG2 constant region lacks the ability to activate complement by the classical pathway or to mediate antibody-dependent cellular cytotoxicity. The IgG4 constant region lacks the ability to activate complement by the classical pathway and mediates antibody-dependent cellular cytotoxicity only weakly. Antibodies essentially lacking these effector functions may be termed 'non-lytic' antibodies.

Human Antibodies

Human antibodies may be produced by a number of methods known to those of skill in the art. Human antibodies can be made by the hybridoma method using human myeloma or mouse-human heteromyeloma cells lines see Kozbor J. Immunol 133, 3001, (1984) and Brodeur, Monoclonal Antibody Production Techniques and Applications, pp 51-63 (Marcel Dekker Inc, 1987). Alternative methods include the use of phage libraries or transgenic mice both of which utilize human V region repertoires (see Winter G, (1994), Annu Rev. Immunol 12, 433-455, Green L L (1999), J. Immunol. methods 231, 11-23).

Several strains of transgenic mice are now available wherein their mouse immunoglobulin loci has been replaced with human immunoglobulin gene segments (see Tomizuka K, (2000) PNAS 97,722-727; Fishwild D. M (1996) Nature Biotechnol. 14,845-851, Mendez M J, 1997, Nature Genetics, 15,146-156). Upon antigen challenge such mice are capable of producing a repertoire of human antibodies from which antibodies of interest can be selected.

Of particular note is the Trimera™ system (see Eren R et al, (1998) Immunology 93:154-161) where human lymphocytes are transplanted into irradiated mice, the Selected Lymphocyte Antibody System (SLAM, see Babcook et al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et al (1994) EMBO 13:3245-3260. According to this technique antibody V domain genes are cloned in frame into either a major or minor coat of protein gene of a filamentous bacteriophage such as M13 or fd and displayed (usually with the aid of a helper phage) as functional antibody fragments on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J. Mol. Bio. 222,581-597, 1991). Where an intact human antibody is desired comprising a Fc domain it is necessary to redone the phage displayed derived fragment into a mammalian expression vectors comprising the desired constant regions and establishing stable expressing cell lines.

The technique of affinity maturation (Marks; Bio/technol 10,779-783 (1992)) may be used to improve binding affinity wherein the affinity of the primary human antibody is improved by sequentially replacing the H and L chain V regions with naturally occurring variants and selecting on the basis of improved binding affinities. Variants of this technique such as "epitope imprinting" are now also available see WO 93/06213. See also Waterhouse; Nucl. Acids Res 21, 2265-2266 (1993).

Chimaeric and Humanised Antibodies

The use of intact non-human antibodies in the treatment of human diseases or disorders carries with it the now well established problems of potential immunogenicity especially upon repeated administration of the antibody that is the immune system of the patient may recognise the non-human intact antibody as non-self and mount a neutralising response. In addition to developing fully human antibodies (see above) various techniques have been developed over the years to overcome these problems and generally involve reducing the composition of non-human amino acid sequences in the intact therapeutic antibody whilst retaining the relative ease in obtaining non-human antibodies from an immunised animal e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chain variable regions of the antibody of the invention. Hybridoma cells serve as a typical source of such DNA. Once isolated, the DNA is placed into expression vectors which are then transfected into host cells such as E. Coli, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984). Thus another embodiment of the invention there is provided a chimaeric antibody comprising a $V_H$ domain having the sequence: SEQ ID No:2, 6, or 10 and a $V_L$ domain having the sequence: SEQ ID No: 4, 8, or 12 fused to a human constant region (which maybe of a IgG isotype e.g. IgG1).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ("donor" antibodies) onto a suitable human framework ("acceptor framework") and constant regions (see Jones et al (1986) Nature 321,522-525 and Verhoeyen M et al (1988) Science 239, 1534-1536). However, CDR grafting per se may not result in the complete retention of antigen-binding properties and it is frequently found that some framework residues of the donor antibody need to be preserved (sometimes referred to as "backmutations") in the humanised molecule if significant antigen-binding affinity is to be recovered (see Queen C et al (1989) PNAS 86, 10,029-10,033, Co, Met at (1991) Nature 351, 501-502). In this case, human V regions showing the greatest sequence homology (typically 60% or greater) to the non-human donor antibody maybe chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody maybe used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E. et al (1994) in *Handbook of Experimental Pharmacology vol.* 113: *The pharmacology of monoclonal Antibodies*, Springer-Verlag, pp 105-134). This procedure of humanisation is referred to as "veneering" because only the surface of the antibody is altered, the supporting residues remain undisturbed. A further alternative approach is set out in WO04/006955. Further alternative approaches include that set out in WO04/006955 and the procedure of Humaneering™ (Kalobios) which makes use of bacterial expression systems and produces antibodies that are close to human germline in sequence (Alfenito-M Advancing Protein Therapeutics January 2007, San Diego, Calif.). Another, approach to humanisation involves selecting human acceptor frameworks on the basis of structural similarity of the human CDR regions to those of the donor mouse antibody CDR regions rather than on homology between other regions of the antibody such as framework regions. This process is also known as Superhumanisation™ (Evogenix Inc.; Hwang et al (2005) Methods 36:35-42).

It will be apparent to those skilled in the art that the term "derived" is intended to define not only the source in the sense of it being the physical origin for the material but also to define material which is structurally identical to the material but which does not originate from the reference source. Thus "residues found in the donor antibody" need not necessarily have been purified from the donor antibody.

Antibody Fragments

In certain embodiments of the invention there is provided therapeutic antibody which is an antigen binding fragment. Such fragments may be functional antigen binding fragments of intact and/or humanised and/or chimaeric antibodies such as Fab, Fd, Fab', F(ab')$_2$, Fv, ScFv fragments of the antibodies described supra. Fragments lacking the constant region lack the ability to activate complement by the classical pathway or to mediate antibody-dependent cellular cytotoxicity. Traditionally such fragments are produced by the proteolytic digestion of intact antibodies by e.g. papain digestion (see for example, WO 94/29348) but may be produced directly from recombinantly transformed host cells. For the production of ScFv, see Bird et al; (1988) Science, 242, 423-426. In addition, antibody fragments may be produced using a variety of engineering techniques as described below.

Fv fragments appear to have lower interaction energy of their two chains than Fab fragments. To stabilise the association of the $V_H$ and $V_L$ domains, they have been linked with peptides (Bird et al, (1988) Science 242, 423-426, Huston et al, PNAS, 85, 5879-5883), disulphide bridges (Glockshuber et al, (1990) Biochemistry, 29, 1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int. Rev. Immunol 10, 195-217. ScFv may be produced in bacterial cells such as *E. Coli* but are more typically produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams et al (1993) Can. Res 53, 4026-4034 and McCartney et al (1995) Protein Eng. 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to between 3 to 12 residues to form "diabodies", see Holliger et al PNAS (1993), 90, 6444-6448. Reducing the linker still further can result in ScFV trimers ("triabodies", see Kortt et al (1997) Protein Eng, 10, 423-433) and tetramers ("tetrabodies", see Le Gall et al (1999) FEBS Lett, 453, 164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56, 3055-3061). ScFv-Sc-Fv tandems ((ScFV)$_2$) may also be produced by linking two ScFv units by a third peptide linker, see Kurucz et al (1995) J.

Immol. 154, 4576-4582. Bispecific diabodies can be produced through the noncovalent association of two single chain fusion products consisting of $V_H$ domain from one antibody connected by a short linker to the $V_L$ domain of another antibody, see Kipriyanov et al (1998), Int. J. Can 77,763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J. Immunol. Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Lett 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains ($V_H$ and $V_L$) in an orientation preventing intramolecular pairing (tandem diabody, see Kipriyanov et al, (1999) J. Mol. Biol. 293, 41-56). Bispecific F(ab')2 fragments can be created by chemical coupling of Fab' fragments or by heterodimerization through leucine zippers (see Shalaby et al, (1992) J. Exp. Med. 175, 217-225 and Kostelny et al (1992), J. Immunol. 148, 1547-1553). Also available are so-called domain antibodies based on isolated $V_H$ or $V_L$ domains (Domantis Ltd.), see U.S. Pat. No. 6,248,516; U.S. Pat. No. 6,291,158; U.S. Pat. No. 6,172,197.

Heteroconjugate Antibodies

Heteroconjugate antibodies are derivatives which also form an embodiment of the present invention. Heteroconjugate antibodies are composed of two covalently joined antibodies formed using any convenient cross-linking methods. See U.S. Pat. No. 4,676,980.

Other Modifications.

Antibodies of the present invention may also incorporate any other modifications in the constant regions. For example glycosylation of antibodies at conserved positions in their constant regions is known to have a profound effect on antibody function, particularly effector functioning such as those described above, see for example, Boyd et al (1996), Mol. Immunol. 32, 1311-1318. Glycosylation variants of the therapeutic antibodies of the present invention wherein one or more carbohydrate moiety is added, substituted, deleted or modified are contemplated. Introduction of an asparagine-X-serine or asparagine-X-threonine motif creates a potential site for enzymatic attachment of carbonhydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al, Science, (2001) 291, 2344, Wacker et al (2002) Science, 298 1790, Davis et al (2002) Chem. Rev. 102, 579, Hang et al (2001) Acc. Chem. Res 34, 727. Thus the invention concerns a plurality of therapeutic antibodies (which maybe of the IgG isotype, e.g. IgG1) as described herein comprising a defined number (e.g. 7 or less, for example 5 or less such as two or a single) glycoform(s) of said antibodies.

Derivatives according to the invention also include therapeutic antibodies of the invention coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L. et al (2000) Int. J. Pharmaceut. 198:83-95. A particular embodiment comprises an antigen-binding fragment of the invention without the effector functions of a) activation of complement by the classical pathway; and b) mediating antibody-dependent cellular cytotoxicity; (such as a Fab fragment or a scFv) coupled to PEG.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies of the invention may be carried out depending on the desired effector property. In particular, human constant regions which essentially lack the functions of a) activation of complement by the classical pathway; and b) mediating antibody-dependent cellular cytotoxicity include the IgG4 constant region, the IgG2 constant region and IgG1 constant regions containing specific mutations as for example mutations at positions 234, 235, 236, 237, 297, 318, 320 and/or 322 disclosed in EP0307434 (WO8807089), EP 0629 240 (WO9317105) and WO 2004/014953. Mutations at residues 235 or 237 within the CH2 domain of the heavy chain constant region (Kabat numbering; EU Index system) have separately been described to reduce binding to FcγRI, FcγRII and FcγRIII binding and therefore reduce antibody-dependent cellular cytotoxicity (ADCC) (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168). Further, some reports have also described involvement of some of these residues in recruiting or mediating complement dependent cytotoxicity (CDC) (Morgan et al., 1995; Xu et al., Cell. Immunol. 2000; 200:16-26; Hezareh et al., J. Virol. 2001, 75 (24); 12161-12168). Residues 235 and 237 have therefore both been mutated to alanine residues (Brett et al. Immunology 1997, 91; 346-353; Bartholomew et al. Immunology 1995, 85; 41-48; and WO9958679) to reduce both complement mediated and FcγR-mediated effects. Antibodies comprising these constant regions may be termed 'non-lytic' antibodies.

One may incorporate a salvage receptor binding epitope into the antibody to increase serum half life see U.S. Pat. No. 5,739,277.

There are five currently recognised human Fcγ receptors, FcγR (I), FcγRIIa, FcγRIIb, FcγRIIIa and neonatal FcRn. Shields et al, (2001) J. Biol. Chem 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in protecting IgG molecules from degradation and thus enhancing serum half life and the transcytosis across tissues (see Junghans R. P (1997) Immunol. Res 16. 29-57 and Ghetie et al (2000) Annu Rev. Immunol. 18, 739-766). Human IgG1 residues determined to interact directly with human FcRn includes Ile253, Ser254, Lys288, Thr307, Gln311, Asn434 and His435.

The therapeutic antibody of the invention may incorporate any of the above constant region modifications.

2. Production Methods

Antibodies of the present invention may be produced in transgenic organisms such as goats (see Pollock et al (1999), J. Immunol. Methods 231:147-157), chickens (see Morrow K J J (2000) Genet. Eng. News 20:1-55), mice (see Pollock et al ibid) or plants (see Doran P M, (2000) Curr. Opinion Biotechnol. 11, 199-204, Ma J K-C (1998), Nat. Med. 4; 601-606, Baez J et al, BioPharm (2000) 13: 50-54, Stoger E et al; (2000) Plant Mol. Biol. 42:583-590). Antibodies may also be produced by chemical synthesis. However, antibodies of the invention are typically produced using recombinant cell culturing technology well known to those skilled in the art. A polynucleotide encoding the antibody is isolated and inserted into a replicable vector such as a plasmid for further cloning (amplification) or expression in a host cell. One useful expression system is a glutamate synthetase system (such as sold by Lonza Biologics), particularly where the host cell is CHO or NS0 (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g. by transformation, transfection, electroporation or transduction) into the same host cell concurrently or sequentially or, if desired both the heavy chain and light chain can be inserted into the same vector prior to such introduction.

It will be immediately apparent to those skilled in the art that due to the redundancy of the genetic code, alternative polynucleotides to those disclosed herein are also available that will encode the polypeptides of the invention.

Signal Sequences

Antibodies of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, a factor leader or acid phosphatase leaders see e.g. WO90/13646. In mammalian cell systems, viral secretory leaders such as herpes simplex gD signal and a native immunoglobulin signal sequence (such as human Ig heavy chain) are available. Typically the signal sequence is ligated in reading frame to polynucleotide encoding the antibody of the invention.

Origin of Replication

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the origin of replication component is not needed for integrated mammalian expression vectors, unless vector propagation is required in E. Coli. However the SV40 on may be used since it contains the early promoter.

Selection Marker

Typical selection genes encode proteins that (a) confer resistance to antibiotics or other toxins e.g. ampicillin, neomycin, methotrexate or tetracycline or (b) complement auxotrophic deficiencies or supply nutrients not available in the complex media or (c) combinations of both. The selection scheme may involve arresting growth of the host cells that contain no vector or vectors. Cells, which have been successfully transformed with the genes encoding the therapeutic antibody of the present invention, survive due to e.g. drug resistance conferred by the co-delivered selection marker. One example is the DHFR-selection system wherein transformants are generated in DHFR negative host strains (eg see Page and Sydenham 1991 Biotechnology 9: 64-68). In this system the DHFR gene is co-delivered with antibody polynucleotide sequences of the invention and DHFR positive cells then selected by nucleoside withdrawal. If required, the DHFR inhibitor methotrexate is also employed to select for transformants with DHFR gene amplification. By operably linking DHFR gene to the antibody coding sequences of the invention or functional derivatives thereof, DHFR gene amplification results in concomitant amplification of the desired antibody sequences of interest. CHO cells are a particularly useful cell line for this DHFR/methotrexate selection and methods of amplifying and selecting host cells using the DHFR system are well established in the art see Kaufman R. J. et al J. Mol. Biol. (1982) 159, 601-621, for review, see Werner R G, Noe W, Kopp K, Schluter M, "Appropriate mammalian expression systems for biopharmaceuticals", Arzneimittel-Forschung. 48(8):870-80, 1998 August. A further example is the glutamate synthetase expression system (Lonza Biologics). A suitable selection gene for use in yeast is the trp1 gene; see Stinchcomb et al Nature 282, 38, 1979.

Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase, among others. Inducible yeast promoters include alcohol dehydrogenase 2, isocytochrome C, acid phosphatase, metallothionein and enzymes responsible for nitrogen metabolism or maltose/galactose utilization, among others.

Promoters for expression in mammalian cell systems include RNA polymerase II promoters including viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1alpha (Mizushima and Nagata Nucleic Acids Res 1990 18(17):5322, among others. The choice of promoter may be based upon suitable compatibility with the host cell used for expression.

Enhancer Element

Where appropriate, e.g. for expression in higher eukaroytics, additional enhancer elements can included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaroytic cell virus such as SV40 enhancer, cytomegalovirus early promoter enhancer, polyoma enhancer, baculoviral enhancer or murine IgG2a locus (see WO04/009823). Whilst such enhancers are typically located on the vector at a site upstream to the promoter, they can also be located elsewhere e.g. within the untranslated region or downstream of the polydenalytion signal. The choice and positioning of enhancer may be based upon suitable compatibility with the host cell used for expression.

Polyadenylation/Termination

In eukaryotic systems, polyadenylation signals are operably linked to polynucleotide encoding the antibody of this invention. Such signals are typically placed 3' of the open reading frame. In mammalian systems, non-limiting example signals include those derived from growth hormones, elongation factor-1 alpha and viral (eg SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic system polyadenylation signals are typically not required and it is instead usual to employ shorter and more defined terminator sequences. The choice of polyadenylation/termination sequences may be based upon suitable compatibility with the host cell used for expression, Other Methods/Elements for Enhanced Yields In addition to the above, other features that can be employed to enhance yields include chromatin remodelling elements, introns and host-cell specific codon modification. The codon usage of the antibody of this invention thereof can be modified to accommodate codon bias of the host cell such to augment transcript and/or product yield (eg Hoekema A et al Mol Cell Biol 1987 7(8):2914-24). The choice of codons may be based upon suitable compatibility with the host cell used for expression.

Host Cells

Suitable host cells for cloning or expressing vectors encoding antibodies of the invention are, for example, prokaroytic, yeast or higher eukaroytic cells. Suitable prokaryotic cells include eubacteria e.g. enterobacteriaceae such as *Escherichia* e.g. *E. Coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as Bacilli such as *B. subtilis* and *B. licheniformis* (see DD 266 710), *Pseudomonas* such as *P. aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183,070, see also Peng et al J. Biotechnol. 108 (2004) 185-192), *Candida,* *Trichoderma reesia* (EP244, 234), Penicillin, *Tolypocladium* and *Aspergillus* hosts such as *A. nidulans* and *A. niger* are also contemplated.

Although Prokaryotic and yeast host cells are specifically contemplated by the invention, typically however, host cells of the present invention are vertebrate cells. Suitable vertebrate host cells include mammalian cells such as COS-1 (ATCC No. CRL 1650) COS-7 (ATCC CRL 1651), human embryonic kidney line 293, PerC6 (Crucell), baby hamster kidney cells (BHK) (ATCC CRL.1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al, (1986) ibid), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Thus in one embodiment of the invention there is provided a stably transformed host cell comprising a vector encoding a heavy chain and/or light chain of the therapeutic antibody as described herein. Typically such host cells comprise a first vector encoding the light chain and a second vector encoding said heavy chain.

Such host cells may also be further engineered or adapted to modify quality, function and/or yield of the antibody of this invention. Non-limiting examples include expression of specific modifying (eg glycosylation) enzymes and protein folding chaperones.

Cell Culturing Methods.

Host cells transformed with vectors encoding the therapeutic antibodies of the invention may be cultured by any method known to those skilled in the art. Host cells may be cultured in spinner flasks, shake flasks, roller bottles or hollow fibre systems but it is preferred for large scale production that stirred tank reactors or bag reactors (eg Wave Biotech, Somerset, N.J. USA) are used particularly for suspension cultures. Typically the stirred tankers are adapted for aeration using e.g. spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly vertebrate host cells may utilise a variety of operational modes such as batch, fed-batch, repeated batch processing (see Drapeau et al (1994) cytotechnology 15: 103-109), extended batch process or perfusion culture. Although recombinantly transformed mammalian host cells may be cultured in serum-containing media such media comprising fetal calf serum (FCS), it is preferred that such host cells are cultured in synthetic serum-free media such as disclosed in Keen et al (1995) Cytotechnology 17:153-163, or commercially available media such as ProCHO-CDM or UltraCHO™ (Cambrex NJ, USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g.

Scharfenberg K et al (1995) in *Animal Cell technology: Developments towards the 21st century* (Beuvery E. C. et al eds), pp 619-623, Kluwer Academic publishers).

Antibodies of the invention secreted into the media may be recovered and purified from the media using a variety of techniques to provide a degree of purification suitable for the intended use. For example the use of therapeutic antibodies of the invention for the treatment of human patients typically mandates at least 95% purity as determined by reducing SDS-PAGE, more typically 98% or 99% purity, when compared to the culture media comprising the therapeutic antibodies. In the first instance, cell debris from the culture media is typically removed using centrifugation followed by a clarification step of the supernatant using e.g. microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (typically monoclonal) preparation comprising at least 10 mg/ml or greater e.g. 100 mg/ml or greater of the antibody of the invention is provided and therefore forms an embodiment of the invention. Concentration to 100 mg/ml or greater can be generated by ultracentrifugation. Suitably such preparations are substantially free of aggregated forms of antibodies of the invention.

Bacterial systems are particularly suited for the expression of antibody fragments. Such fragments are localised intracellularly or within the periplasma. Insoluble periplasmic proteins can be extracted and refolded to form active proteins according to methods known to those skilled in the art, see Sanchez et al (1999) J. Biotechnol. 72, 13-20 and Cupit P M et al (1999) Lett Appl Microbiol, 29, 273-277.

3. Pharmaceutical Compositions and Mode of Administration

Purified preparations of antibodies of the invention as described supra, may be incorporated into pharmaceutical compositions for use in the treatment of human diseases and disorders such as those outlined above. Typically such compositions further comprise a pharmaceutically acceptable (i.e. inert) carrier as known and called for by acceptable pharmaceutical practice, see e.g. Remingtons Pharmaceutical Sciences, 16th ed, (1980), Mack Publishing Co. Examples of such carriers include sterilised carrier such as saline, Ringers solution or dextrose solution, buffered with suitable buffers to a pH within a range of 5 to 8. Pharmaceutical compositions for injection (e.g. by intravenous, intraperitoneal, intradermal, subcutaneous, intramuscular or intraportal) or continuous infusion are suitably free of visible particulate matter and may comprise from 0.1 mg to 10 g of therapeutic antibody, typically between 5 mg and 25 mg of antibody. Methods for the preparation of such pharmaceutical compositions are well known to those skilled in the art. In one embodiment, pharmaceutical compositions comprise from 0.1 mg to 10 g of therapeutic antibodies of the invention in unit dosage form, optionally together with instructions for use. Pharmaceutical compositions of the invention may be lyophilised (freeze dried) for reconstitution prior to administration according to methods well known or apparent to those skilled in the art. Where embodiments of the invention comprise antibodies of the invention with an IgG1 isotype, a chelator of copper such as citrate (e.g. sodium citrate) or EDTA or histidine may be added to the pharmaceutical composition to reduce the degree of copper-mediated degradation of antibodies of this isotype, see EP0612251.

Effective doses and treatment regimes for administering the antibody of the invention are generally determined empirically and are dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York but will in general be between 0.1 mg and 1 g. In one embodiment, the dosing regime for treating a human patient is 0.1 mg to 10 g of therapeutic antibody of the invention administered subcutaneously once per week or every two weeks, or by intravenous infusion every 1 or 2 months. Compositions of the present invention may also be used in prophylatically.

4. Clinical Uses.

The present invention relates to an antibody which binds to human IL-8, Gro-alpha, Gro-beta, Gro-gamma, and ENA-78 The present invention also concerns methods of treating diseases or disorders characterised by elevated or unbalanced level of one or more of human IL-8, Gro-alpha, Gro-beta, Gro-gamma, and ENA-78, particularly, COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, and/or endometriosis with said antibody, pharmaceutical compositions comprising said antibody and methods of manufacture.

The present invention also relates to use of an antibody in the manufacture of a medicament for the treatment of diseases or disorders characterised by elevated or unbalanced level of one or more of human IL-8, Gro-alpha, Gro-beta, Gro-gamma, GCP-2 and ENA-78, particularly COPD, osteoarthritis, rheumatoid arthritis, erosive arthritis, asthma, atherosclerosis, inflammatory bowel disease, psoriasis, transplant rejection, gout, cancer, acute lung injury, acute lung disease, sepsis, ARDS, peripheral artery disease, systemic sclerosis, neonatal respiratory distress syndrome, exacerbation of asthma and COPD, cystic fibrosis, diffuse panbronchiolitis, reperfusion injury, or endometriosis. Although the present invention has been described principally in relation to the treatment of human diseases or disorders, the present invention may also have applications in the treatment of similar diseases or disorders in non-human mammals.

Specific Embodiments

EXAMPLE 1

Generation of Mouse Monoclonal Antibody 656.35, 197.2, and 81.1

Generation of a Penta-Specific mAb Against the Target Chemokines (Human IL-8, Gro-Alpha, Gro-Beta, Gro-Gamma, and ENA-78).

Multiple methods and schemes were used to immunize mice in an attempt to generate pan-specific mAbs. The generation of pan-specific mAbs were generated using various mixtures of multiple antigenic peptides (MAPs) and/or intact target chemokines (IL-8, Gro-α, -β, -γ, and ENA-78) mixed in complete or incomplete Freund's Adjuvant (cFA or iFA), following a modified Repetitive Immunization Multiple Sites (RIMMS) protocol in the SJL/JOrlCrl mouse strain.

MAPs or multiple antigenic peptides serve two functions within the immunization protocol. First, MAPs allow for a selective multiple presentation of a known target amino acid sequence. Secondly, there is an increase in mass, due to multiple copies of the sequence linked, for example, via a lysine core, which also increases the immunogenicity of the sequence over that of individual peptides (Francis, J. P., et al., Immunology, 1991: 73; 249, Schott, M. E., et al., Cell. Immuno. 1996: 174: 199-209, Tam, J. P. Proc. Natl. Acad. Sci. 1988: 85; 5409-5413). FIG. 1 is a schematic drawing of a set of MAPs having amino acid sequences SEQ ID NOs:49-53. A linker in MAPs can be any linker other than lysines.

General Immunization Time Line:

Two different immunization protocols following the above time line produced pan-specific mAbs:
1. Initial immunization (day 0) consists of multiple subcutaneous injections (hind quarters, back and neck) of all target chemokines mixed in cFA (10 μg each). The following 4 boosts consisted of a mixture of all the target chemokines mixed in iFA (10 μg each). The fifth and all subsequent boosts consisted of a cocktail of all the target chemokines and all 5 linear MAPs (10 μg each) in iFA. The final boost 3 days prior to sacrifice and fusion consisted of all the target chemokines and linear MAPs in PBS and was delivered via an intraperitoneal (IP) injection.
2. Initial immunization (day 0) consists of multiple subcutaneous injections (hind quarters, back and neck) of all five linear MAPs mixed in cFA (10 μg each). The following 4 boosts consisted of a mixture of all five linear MAPs in iFA (10 μg each). The fifth and all subsequent boosts consisted of a cocktail of all the all 5 linear MAPs and all target chemokines (10 μg each) in iFA. The final boost 3 days prior to sacrifice and fusion consisted of all the all 5 linear MAPs and all target chemokines (10 μg each) in PBS and was delivered via an intraperitoneal (IP) injection.

EXAMPLE 2

Pan-Binding of the mAb to the Target Chemokines (Human IL-8, Gro-Alpha, Gro-Beta, Gro-Gamma, GCP-2, and ENA-78) has been Confirmed Via a Time-Resolved Fluorescence Immunofluorescent Assay (TRFIA)

Briefly, each antigen (human IL-8, Gro-alpha, Gro-beta, Gro-gamma, GCP-2, and ENA-78, and hIL-18 when used as negative control) is individually coated onto a 96-well immunofluorescent plate. The plates are then washed and blocked with a commercially available blocking solution. Blocking solution is emptied and samples containing the mAb are added into each well and incubated for 40 to 60 minutes (this allows the mAb to bind to the target chemokines). The plates are then washed again and a detection Ab is added to each well. Detection reagents were as follows for 2×656.35, chimera (HcLc) and humanized MAbs respectively: biotinylated anti-mouse IgG, biotinylated anti-human IgG Fab2 reagent, and europium anti-human IgG. The detection antibody is conjugated to either europium or biotin. Following another round of washing, to remove unbound detection Ab, a solution of streptavidin-europium was added to biotin detected assays. Streptavidin-europium binds to the biotin allowing for detection. After a final wash to remove unbound streptavidin-europium, or in the case of the humanized MAb assay after the europium conjugate secondary is washed, each well is filled with a chelating detergent solution to activate the europium producing fluorescence. The greater the fluorescence recorded is directly proportionate to the amount of detection Ab present in the well which is directly linked and proportionate to the amount of the chemokine binding mAb.

Figure 5A:
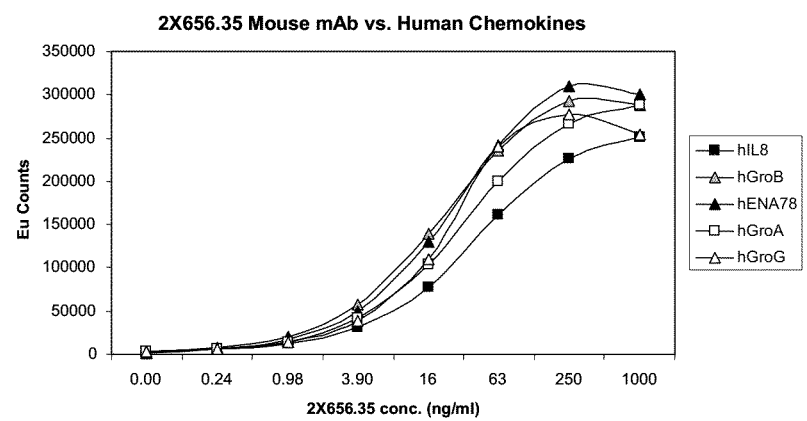
FIG. 5A shows mouse 656.35 mAb binding to target human chemokines
Figure 5B:
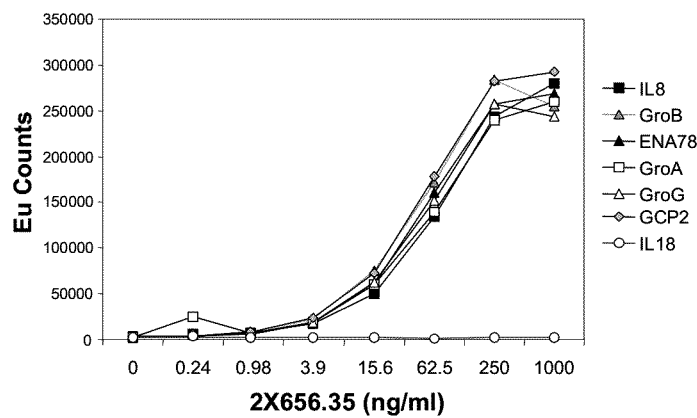
FIG. 5B shows the Chimera Antibody (HcLc) mAb binding to human target chemokines
Figure 5C:
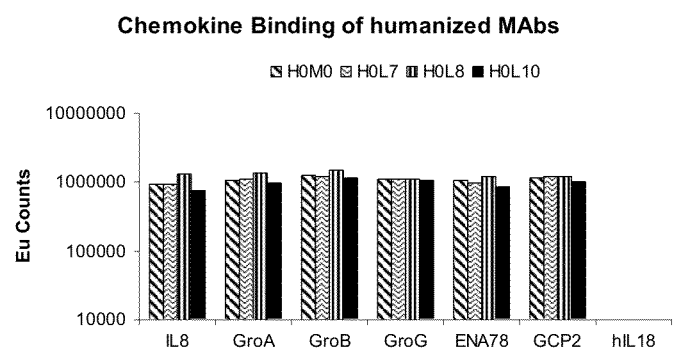
FIG. 5C shows humanized mAbs binding to human target chemokines

FIG. 5A shows mouse 656.35 mAb binding to target human chemokines FIG. 5B shows the Chimera Antibody (HcLc) mAb binding to human target chemokines FIG. 5C shows humanized mAbs binding to human target chemokines.

EXAMPLE 3

Functional Pan-Inhibition by Murine mAb was Confirmed Using a Variety of Methods: CXCR2 Mediated $Ca^{2+}$ Mobilization, Human Neutrophil Chemotaxis, and Human Neutrophil Activation (CD11b Surface Expression)

A microtiter plate based calcium mobilization assay, FLIPR (Fluorometric Imaging Plate Reader, Molecular Devices, Sunnyvale Calif., [Schroeder, 1996]), was used for the functional characterization of the neutralizing effect of antibodies on ELR+ chemokine induced $[Ca^{2+}]i$-mobilization in CHO-K1 cells transfected with and stably expressing hCXCR2 and Gα16.

On the day prior to assay, cells were plated in 96 well, blackwall, clear bottom plates (Packard View) at a concentration of 40000 cells per well. After 18 to 24 hours, media was aspirated off cells and replaced with 100 μl load media containing Eagles Minimal Essential Medium (EMEM) with Earl's salts and L-Glutamine, 0.1% BSA (Serologicals Corporation), 4 μM Fluo-4-acetoxymethyl ester fluorescent indicator dye (Fluo-4 AM) and 2.5 mM probenecid. Cells were incubated in this dye containing media for 1 hour at 37° C. The dye containing media was then aspirated off the cells and replaced with identical media without Fluo-4 AM and with 0.1% Gelatin (BSA removed) and 2.5 mM probenecid. Cells were incubated for 10 min. at 37° C. and then washed 3 times with KRH assay buffer [Krebs Ringer Henseleit (120 mM NaCl, 4.6 mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES (pH 7.4)) with 0.1% gelatin and 2.5 mM probenecid]. After the final buffer wash, 100 μl KRH assay buffer with 0.1% gelatin and 2.5 mM probenecid was added to cells and warmed to 37° C. for 10 min. before being placed in FLIPR where dye loaded cells were exposed to excitation light (488 nm) from a 6 watt Argon Laser. $[Ca^{2+}]i$-mobilization was monitored as a result of an increase in 516 nm emission intensity of Fluo-4 when bound to $Ca^{2+}$. Change in emission intensity is directly related to cytosolic calcium levels, $[Ca^{2+}]i$. After monitoring baseline for 10 sec., 50 μl of 3×ELR+ chemokine, which had been pre-incubated with a concentration range of antibody, was added to the cell plate and data collected every sec. for 1 min., followed by an additional half min. of recording in 3 sec. intervals. Maximal cellular response above basal reading was exported for plotting in GraphPad Prism (v4.03).

The $IC_{50}$ was defined as the concentration of antibody required, during pre-treatment of 3× $EC_{80}$ chemokine, to neutralize the CXCR2 mediated stimulatory effect of an $EC_{80}$ concentration of the ELR+ chemokine by 50%. A secondary cellular response to 25 μM ATP was monitored to test cell viability [Sarau, 1999].

TABLE

Inhibition of human ELR+ chemokine induced calcium flux (geometrically meaned IC50, ug/ml) by three murine mAb. (n = 3 to 6)

| murine mAB | 3 nM hIL-8 | | 10 nM hGROα | | 6 nM hGROβ | | 30 nM hENA-78 | | 100 nM hGCP-2 | |
|---|---|---|---|---|---|---|---|---|---|---|
| | $IC_{50}$ (ug/ml) | 95% C.I. | $IC_{50}$ (ug/ml) | 95% C.I. | $IC_{50}$ (ug/ml) | 95% C.I. | $IC_{50}$ (ug/ml) | 95% C.I. | $IC_{50}$ (ug/ml) | 95% C.I. |
| 656.35 | 0.18 | 0.14-0.25 | 1.43 | 0.60-3.42 | 1.06 | 0.78-1.42 | 2.09 | 0.71-6.14 | 9.58 | 1.17-78.57 |
| 81.1 | 67.65 | 18.80-243.50 | 0.94 | 0.37-2.38 | n.d. | N/A | 1.84 | 0.69-4.93 | 9.11 | 1.44-57.61 |
| 197.2 | 2.19 | 0.61-7.88 | 2.24 | 0.39-12.98 | n.d. | N/A | 13.86 | 1.71-112.49 | >157 | N/A |

(n.d. = not determined, N/A = not available)

Schroeder K S, Neagle, B D. FLIPR: a new instrument for accurate, high throughput optical screening. *J. Biomol. Screen.* 1996:1-75.

Sarau H M, Ames R S, Chambers J, Ellis C, Elshourbagy N, Foley J J et al. Identification, molecular cloning, expression, and characterization of a cysteinyl leukotrien receptor. *Mol Pharmacol.* 1999; 56:657-663.

Inhibition of IL-8 stimulated human neutrophil chemotaxis was also demonstrated using a micro-Boyden chamber. The micro-Boyden apparatus consists of two small chambers one above and one below a 3 micron-porous membrane. The lower chamber is loaded with the chemotaxic agent (i.e. IL-8) or a mixture of the chemokine with the penta-specific mAb. The upper chamber contains purified non-activated human neutrophils. Once the chamber is assembled a concentration gradient is formed from the bottom well to the upper, stimulating the neutrophils to chemotax across the membrane. The assay is expressed as a CI (chemotactic index) which is a ratio of the number of cells which chemotax in response to a stimulant over non-stimulated chemotaxic cell number. Pre-incubating the chemokine (i.e. IL-8) with the penta-specific mAb in the lower chamber, dose dependently inhibited IL-8 stimulated neutrophil chemotaxis. IL-8 at 10 nM achieved a CI of 3.6±0.8. Pre-incubation of IL-8 with increasing concentrations of the penta-specific mAb (656.35) dose dependently inhibited human neutrophil chemotaxis, significance was reached at CI of 2.2±0.6 at 1 μg/ml. Due to the amounts and sensitivity of the assay the other chemokines were unable to be examined (Gro-α, -β, -γ, and ENA-78).

Inhibition of purified human neutrophil activation via monitoring surface expression of CD11b. CD11b or Mac-1 mediates adhesion to substrates, aggregation and chemotaxis and is known to be up-regulated on the surface activated neutrophils (Molad, Y., J., et al., Clin. Immunol. Immunopathol. 1994: 71; 281-286). Briefly, non-activated human neutrophils are purified and ex vivo stimulated with either target chemokines (i.e. IL-8) or with chemokines pre-incubated with a chemokine penta-specific mAb. Data are presented as percent activation set to the maximal CD11b surface expression due to IL-8 stimulation. Pre-incubation of IL-8 with the 656.35 mAb dose dependently inhibited increased levels of surface expression of CD11b and thus indicates inhibition of neutrophil activation (79.9%±3.7, 48.5%±7.2, 28.7%±3.2, and 31.6%±3.4, at 0.01, 0.1, 1, 10 and 50 μg/ml respectively).

EXAMPLE 4

Penta-Specific mAbs Association/Dissociation Values for Each Target Chemokine (Human IL-8, Gro-Beta, and ENA-78)

Methods for Biacore Analysis.

For experiment designated KL, rabbit anti mouse IgG-Fc (Biacore BR-1005-14) is immobilized on a CM5 chip by primary amine coupling in accordance with the manufactures instructions.

For experiment designated BE, purified antibodies directly immobilized to the chip by amine coupling was used.

Supernatant or purified antibody from parental mouse mAb is captured on the anti-mouse IgG-Fc surface. Defined concentrations of each analyte (IL8, Gro-band ENA-78) are passed over the immobilized or captured antibody surface, a separate capture event is used for each analyte injection. After each injection of analyte the surface is regenerated by injection of a mild acidic solution, which removes the captured antibody but does not significantly affect the capability anti mouse IgG-Fc surface to perform another capture event nor does it affect the directly immobilized antibodies. An injection of buffer is also injected over the antibody captured surface and this is used for double referencing. The data is analyzed using the analysis software inherent to the machine, using the 1:1 model of binding.

| | | IL-8 | | | Gro-B | | | ENA-78 | | |
|---|---|---|---|---|---|---|---|---|---|---|
| | mAb | kd | ka | KD | kd | ka | KD | kd | ka | KD |
| KL | 656.35 | 1.48E-03 | 1.53E+06 | 9.64E-10 | 2.01E-03 | 3.82E+06 | 5.26E-10 | 1.87E-03 | 1.07E+06 | 1.74E-09 |
| BE | | 6.87E-04 | 8.19E+06 | 8.39E-11 | 1.46E-03 | 1.32E+07 | 1.11E-10 | 7.96E-04 | 2.94E+06 | 2.71E-10 |
| KL | 81.1 | 9.32E-03 | 1.95E+06 | 4.80E-09 | 3.12E-04 | 2.76E+06 | 1.13E-10 | 3.76E-04 | 6.11E+05 | 6.16E-10 |
| BE | | 1.08E-01 | 1.95E+06 | 5.55E-08 | 4.89E-04 | 5.44E+06 | 8.98E-11 | 3.94E-06 | 1.65E+05 | 2.39E-11 |
| KL | 197.2 | 3.69E-03 | 6.27E+05 | 5.89E-09 | 9.93E-04 | 1.55E+05 | 6.39E-10 | 2.69E-03 | 2.99E+05 | 9.00E-09 |
| BE | | 4.99E-04 | 7.23E+05 | 6.90E-10 | 4.80E-08 | 1.04E+06 | 4.62E-14 | 3.02E-03 | 3.01E+05 | 1.01E-08 |

EXAMPLE 5

Epitope Mapping 656.35 mAb was epitope mapped and found to bind within KELRCQCIKTYSKP (SEQ ID NO: 54) in human IL-8. Thus in another embodiment, the present invention relates to a penta-specific antibody which binds within epitope of SEQ ID NO:54 of human IL-8.

EXAMPLE 6

Efficacy Study of a Chimera Antibody Made from 656.35 Having Heavy Chain Sequence of SEQ ID NO: 56, and Light Chain Sequence of SEQ ID NO:58. (This Antibody Will be Referred to as the Chimera Antibody)

In Vivo Studies:

An inhaled LPS acute lung inflammatory model was used to examine the ability of the a penta-specific antibody to inhibit infiltration of neutrophils into the lungs of non-human primates (NHPs—cynomolgus). Briefly, NHP (non-human primate) were pre-screened for health and responsiveness to exogenously added cynomolgus IL-8 (cynoIL-8). Selected NHP were then subjected to baseline sample collections (blood and bronchoalveolar lavage—BAL) five days prior to the first LPS challenge. LPS challenged consisted of tranquilizing the NHP with a single IM injection of ketamine HCl (~10 mg/kg). Once the NHP is sedated, anesthesia is administered, via an intravenous infusion of propofol (~0.2 mg/kg/min, as necessary). Anesthetized animals are placed on a circulating warm-water heating blanket and/or within a circulating warm-air blanket and an ophthalmic lubricant is administered to each eye. The animals are then intubated and mechanically ventilated for challenge procedure. A volume regulated Positive Pressure ventilator is used during the procedure (Stoelting Cat/Rabbit ventilator www.stoeltingco.com Cat #5019510). Lipopolysaccharide (LPS) challenge is performed via aerosol inhalation using a DeVilbiss Ultraneb-99 ultrasonic nebulizer. Aerosolized LPS is administered for 5 minutes at 100 ug/ml. Heart rate, body temperature, and respiration rate are monitored and recorded during challenge procedures. The initial challenge confirms that the NHP respond to LPS (increased neutrophil infiltration into the lungs and elevated cynoIL-8 levels). Individual NHP responses were confirmed by sample collections at 6 and 24-hours post challenge.

The initial LPS challenged NHP were then randomly divided into two groups. Following a 4-week recovery all participating NHP were subjected to another baseline sample (blood and BAL). Four days post baseline measurements the subject groups received IV injection of either a vehicle or an injection of 1 mg/kg of the Chimera Antibody. The next day the NHP were challenged again with inhaled LPS and samples for analysis were collected 6 and 24-hour post challenge. Following an additional recovery period base line samples were collected from the vehicle NHP, 4 days later these NHP were treated with a single IV bolus injection of the Chimera Antibody at 10 mg/kg. The next day the animals were exposed to an LPS challenge and samples were collected for analysis at 6 and 24 hours.

The LPS inhalation is an acute inflammatory model which stimulates an elevation of chemotactic chemokines such at IL-8, which lead to increased infiltration of neutrophils into the lungs. The primary efficacy parameter for the Chimera Antibody treatment is inhibition of infiltrating neutrophils into the lungs of NHP challenged with LPS. Neutrophil infiltration in this acute inflammatory model occurs during the first 24 hours following LPS challenge at which point other inflammatory processes are becoming more prominent.

Pretreatment of with the Chimera Antibody significantly and dose dependently inhibited neutrophil infiltration into lungs of LPS challenged NHP. Treatment with the Chimera Antibody also prevented elevation of circulating neutrophils, while not affecting the actual neutrophil function, (i.e. the cells ability to phagocytos). Treatment also did not greatly affect other cell types such as macrophages/monocytes in the lung or circulation. See FIG. 2.

EXAMPLE 7

Further Studies on Humanized mAbs

Multiple humanized penta-specific antibody constructs have been produced, four of which have been shown to bind tightly to, and inhibit all target chemokines (For each sequence, see Sequence Information below). This analysis consisted of affinity measurements (BiaCore), calcium mobilization assays (in vitro functional assay, FLIPR), and CD11b human and NHP neutrophil stimulation assay (ex vivo functional assay, flow cytometry).

BiaCore

A Protein A capture method was used to generate kinetics for the humanised and chimeric constructs as follows:
Protein A is immobilised on a CM5 chip by primary amine coupling in accordance with the manufactures instructions. Purified humanised or chimeric antibody is captured on the Protein A surface. After capture defined concentrations of each analyte (IL8, Gro-β and ENA-78) are passed over the antibody captured surface, a separate capture event is used for each analyte injection. After each injection of analyte the surface is regenerated by injection of a mild acidic solution, which removes the captured antibody but does not significantly affect the capability of the Protein A to perform another capture event. An injection of buffer is also injected over the antibody captured surface and this is used for double referencing. The data is analysed using the analysis software inherent to the machine, using the 1:1 model of binding.

| Construct | ka (1/Ms) | kd (1/s) | KD (M) |
|---|---|---|---|
| Measurements with Gro-beta | | | |
| HcLc | 7.39E+06 | 8.16E−04 | 1.11E−10 |
| HcLc | 2.11E+07 | 0.0011 | 5.21E−11 |
| HcLc | 1.59E+07 | 8.88E−04 | 5.57E−11 |
| HcLc | 1.19E+07 | 6.16E−04 | 5.17E−11 |
| HcLc | 1.43E+07 | 5.43E−04 | 3.79E−11 |
| HcLc | 1.33E+07 | 6.76E−04 | 5.09E−11 |
| HcLc | 1.51E+07 | 6.73E−04 | 4.45E−11 |
| HcLc | 1.49E+07 | 6.44E−04 | 4.33E−11 |
| HcLc | 2.54E+07 | 0.001163 | 4.57E−11 |
| HcLc | 1.81E+07 | 0.001058 | 5.85E−11 |
| HcLc | 2.04E+07 | 8.54E−04 | 4.18E−11 |
| HcLc | 1.82E+07 | 5.06E−04 | 2.78E−11 |
| H0L7 | 6.99E+06 | 9.66E−04 | 1.38E−10 |
| H0L7 | 1.76E+07 | 0.001305 | 7.40E−11 |
| H0L7 | 1.63E+07 | 0.001039 | 6.39E−11 |
| H0L7 | 1.14E+07 | 0.005616 | 4.93E−10 |
| H0L7 | 1.20E+07 | 0.004398 | 3.66E−10 |
| H0L7 | 1.42E+07 | 9.57E−04 | 6.73E−11 |

| Construct | ka (1/Ms) | kd (1/s) | KD (M) |
|---|---|---|---|
| H0L7 | 1.76E+07 | 0.00118 | 6.72E−11 |
| H0L7 | 1.63E+07 | 0.001389 | 8.52E−11 |
| H0L7 | 1.12E+07 | 0.008212 | 7.32E−10 |
| H0L7 | 2.63E+07 | 0.001546 | 5.88E−11 |
| H0L7 | 2.10E+07 | 9.28E−04 | 4.41E−11 |
| H0L8 | 1.28E+07 | 0.005462 | 4.27E−10 |
| H0L8 | 1.99E+07 | 0.01065 | 5.36E−10 |
| H0L8 | 1.19E+07 | 0.007727 | 6.52E−10 |
| H0L8 | 1.18E+07 | 0.007799 | 6.60E−10 |
| H0L8 | 1.61E+07 | 0.006903 | 4.29E−10 |
| H0L8 | 1.85E+07 | 0.004586 | 2.48E−10 |
| H0L10 | 1.23E+07 | 0.001395 | 1.13E−10 |
| H0L10 | 1.45E+07 | 0.001261 | 8.68E−11 |
| H0L10 | 1.44E+07 | 0.001477 | 1.03E−10 |
| H0L10 | 1.28E+07 | 0.001394 | 1.09E−10 |
| H0L10 | 1.98E+07 | 0.00144 | 7.28E−11 |
| H0L10 | 1.94E+07 | 0.00109 | 5.62E−11 |
| H0M0 | 1.20E+07 | 0.001394 | 1.17E−10 |
| H0M0 | 1.13E+07 | 0.007071 | 6.24E−10 |
| H0M0 | 1.58E+07 | 0.001708 | 1.08E−10 |
| H0M0 | 1.43E+07 | 0.001829 | 1.28E−10 |
| H0M0 | 1.03E+07 | 0.009588 | 9.34E−10 |
| H0M0 | 1.85E+07 | 0.001728 | 9.35E−11 |
| H0M0 | 1.81E+07 | 0.001252 | 6.91E−11 |
| Measurements with IL8 | | | |
| HcLc | 3.77E+06 | 2.34E−04 | 6.22E−11 |
| HcLc | 1.03E+07 | 2.87E−04 | 2.78E−11 |
| HcLc | 8.20E+06 | 2.76E−04 | 3.37E−11 |
| HcLc | 1.04E+07 | 2.68E−04 | 2.58E−11 |
| HcLc | 9.44E+06 | 2.53E−04 | 2.68E−11 |
| HcLc | 9.97E+06 | 2.30E−04 | 2.31E−11 |
| H0L7 | 2.74E+06 | 2.84E−04 | 1.04E−10 |
| H0L7 | 8.99E+06 | 4.00E−04 | 4.45E−11 |
| H0L7 | 7.64E+06 | 2.84E−04 | 3.71E−11 |
| H0L7 | 5.98E+06 | 0.001167 | 1.95E−10 |
| H0L7 | 8.74E+06 | 3.52E−04 | 4.03E−11 |
| H0L7 | 7.51E+06 | 3.63E−04 | 4.83E−11 |
| H0L7 | 9.10E+06 | 3.89E−04 | 4.28E−11 |
| H0L8 | 5.90E+06 | 0.00111 | 1.88E−10 |
| H0L8 | 7.89E+06 | 0.001126 | 1.43E−10 |
| H0L8 | 6.80E+06 | 0.001193 | 1.75E−10 |
| H0L8 | 7.30E+06 | 0.001112 | 1.52E−10 |
| H0L10 | 6.86E+06 | 4.57E−04 | 6.66E−11 |
| H0L10 | 7.20E+06 | 3.67E−04 | 5.10E−11 |
| H0L10 | 7.21E+06 | 3.96E−04 | 5.48E−11 |
| H0L10 | 7.43E+06 | 3.73E−04 | 5.02E−11 |
| H0M0 | 7.02E+06 | 3.98E−04 | 5.67E−11 |
| H0M0 | 6.40E+06 | 0.001467 | 2.29E−10 |
| H0M0 | 7.96E+06 | 4.09E−04 | 5.14E−11 |
| H0M0 | 7.97E+06 | 4.60E−04 | 5.77E−11 |
| H0M0 | 7.50E+06 | 4.18E−04 | 5.57E−11 |
| Measurements with ENA78 | | | |
| HcLc | 3.67E+06 | 1.70E−04 | 4.63E−11 |
| HcLc | 5.81E+06 | 1.71E−04 | 2.94E−11 |
| HcLc | 5.11E+06 | 1.84E−04 | 3.60E−11 |
| HcLc | 5.28E+06 | 1.54E−04 | 2.91E−11 |
| HcLc | 4.87E+06 | 1.56E−04 | 3.20E−11 |
| HcLc | 4.78E+06 | 1.23E−04 | 2.58E−11 |
| H0L7 | 2.95E+06 | 2.04E−04 | 6.93E−11 |
| H0L7 | 5.28E+06 | 2.97E−04 | 5.63E−11 |
| H0L7 | 4.59E+06 | 2.17E−04 | 4.74E−11 |
| H0L7 | 3.03E+06 | 3.33E−04 | 1.10E−10 |
| H0L7 | 5.11E+06 | 2.58E−04 | 5.04E−11 |
| H0L7 | 4.76E+06 | 3.07E−04 | 6.45E−11 |
| H0L7 | 4.91E+06 | 2.77E−04 | 5.63E−11 |
| H0L8 | 2.88E+06 | 2.88E−04 | 1.00E−10 |
| H0L8 | 2.82E+06 | 2.66E−04 | 9.41E−11 |
| H0L8 | 2.95E+06 | 2.69E−04 | 9.12E−11 |
| H0L8 | 3.29E+06 | 2.48E−04 | 7.55E−11 |
| H0L10 | 4.07E+06 | 3.66E−04 | 8.99E−11 |
| H0L10 | 4.72E+06 | 3.40E−04 | 7.22E−11 |
| H0L10 | 4.20E+06 | 3.12E−04 | 7.42E−11 |
| H0L10 | 4.38E+06 | 2.68E−04 | 6.13E−11 |
| H0M0 | 3.91E+06 | 3.09E−04 | 7.89E−11 |
| H0M0 | 2.97E+06 | 3.49E−04 | 1.17E−10 |
| H0M0 | 4.39E+06 | 3.16E−04 | 7.20E−11 |
| H0M0 | 4.18E+06 | 3.34E−04 | 7.99E−11 |
| H0M0 | 4.52E+06 | 2.94E−04 | 6.51E−11 |

Affinity (KD) is determined by examining the association rate (ka) and disassociation rate (kd) of proteins.

HcLc Refers to Chimera Antibody Made from 656.35 Having Heavy Chain Sequence of SEQ ID NO: 56, and Light Chain Sequence of SEQ ID NO: 58.

Functional Assay: Calcium Mobilization (FLIPR) Using CHO-K1 CXCR2 (w/G α16)

A microtiter plate based calcium mobilization assay, FLIPR (Fluorometric Imaging Plate Reader, Molecular Devices, Sunnyvale Calif., [Schroeder, 1996]), was used for the functional characterization of the neutralizing effect of antibodies on ELR+ chemokine induced $[Ca^{2+}]$i-mobilization in CHO-K1 cells transfected with and stably expressing hCXCR2 and Gα16.

On the day prior to assay, cells were plated in 96 well, blackwall, clear bottom plates (Packard View) at a concentration of 40000 cells per well. After 18 to 24 hours, media was aspirated off cells and replaced with 100 µl load media containing Eagles Minimal Essential Medium (EMEM) with Earl's salts and L-Glutamine, 0.1% BSA (Serologicals Corporation), 4 µM Fluo-4-acetoxymethyl ester fluorescent indicator dye (Fluo-4 AM) and 2.5 mM probenecid. Cells were incubated in this dye containing media for 1 hour at 37° C. The dye containing media was then aspirated off the cells and replaced with identical media without Fluo-4 AM and with 0.1% Gelatin (BSA removed) and 2.5 mM probenecid. Cells were incubated for 10 min. at 37° C. and then washed 3 times with KRH assay buffer [Krebs Ringer Henseleit (120 mM NaCl, 4.6 mM KCl, 1.03 mM $KH_2PO_4$, 25 mM $NaHCO_3$, 1.0 mM $CaCl_2$, 1.1 mM $MgCl_2$, 11 mM Glucose, 20 mM HEPES (pH 7.4)) with 0.1% gelatin and 2.5 mM probenecid]. After the final buffer wash, 100 µl KRH assay buffer with 0.1% gelatin and 2.5 mM probenecid was added to cells and warmed to 37° C. for 10 min. before being placed in FLIPR where dye loaded cells were exposed to excitation light (488 nm) from a 6 watt Argon Laser. $[Ca^{2+}]$i-mobilization was monitored as a result of an increase in 516 nm emission intensity of Fluo-4 when bound to $Ca^{2+}$. Change in emission intensity is directly related to cytosolic calcium levels, $[Ca^{2+}]$i. After monitoring baseline for 10 sec., 50 µl of 3×ELR+ chemokine, which had been pre-incubated with a concentration range of antibody, was added to the cell plate and data collected every sec. for 1 min., followed by an additional half min. of recording in 3 sec. intervals. Maximal cellular response above basal reading was exported for plotting in GraphPad Prism (v4.03).

The $IC_{50}$ was defined as the concentration of antibody required, during pre-treatment of 3× $EC_{80}$ chemokine, to neutralize the CXCR2 mediated stimulatory effect of an $EC_{80}$ concentration of the ELR+ chemokine by 50%. A secondary cellular response to 25 µM ATP was monitored to test cell viability [Sarau, 1999].

TABLE

Inhibition of human ELR+ chemokine induced calcium flux (geometrically meaned IC50, ug/ml) by four humanized mAb constructs. (n = 3)

| Pre-treated 3X EC$_{80}$ ELR+ Chemokine | H0L7 IC$_{50}$ (ug/ml) | H0L7 95% C.I. | H0L8 IC$_{50}$ (ug/ml) | H0L8 95% C.I. | H0L10 IC$_{50}$ (ug/ml) | H0L10 95% C.I. | H0M0 IC$_{50}$ (ug/ml) | H0M0 95% C.I. |
|---|---|---|---|---|---|---|---|---|
| 3 nM hiL8 | 0.30 | 0.12-0.72 | 0.83 | 0.70-0.98 | 0.19 | 0.15-0.22 | 0.19 | 0.15-0.23 |
| 10 nM hGROa | 1.48 | 0.98-2.23 | 3.52 | 2.74-4.53 | 1.09 | 0.58-2.06 | 1.11 | 0.67-1.83 |
| 6 nM hGROb | 1.04 | 0.19-5.58 | 7.93 | 4.20-14.97 | 0.66 | 0.24-1.86 | 0.99 | 0.35-2.76 |
| 30 nM hENA-78 | 2.48 | 0.78-7.91 | 2.42 | 1.27-4.63 | 1.88 | 0.83-4.26 | 1.75 | 1.33-2.29 |
| 100 nM hGCP-2 | 11.43 | 8.19-15.96 | 40.38 | 38.45-42.41 | 11.54 | 6.30-21.17 | 13.03 | 7.20-23.56 |

Schroeder K S, Neagle, B D. FLIPR: a new instrument for accurate, high throughput optical screening. *J. Biomol. Screen.* 1996:1-75.

Sarau H M, Ames R S, Chambers J, Ellis C, Elshourbagy N, Foley J J et al. Identification, molecular cloning, expression, and characterization of a cysteinyl leukotrien receptor. *Mol Pharmacol.* 1999; 56:657-663.

Ex Vivo CD11b Human Neutrophil Stimulation Assay

Flow cytometry was used to examine the humanized pentaspecific antibodies' ability to prevent chemokine induced human purified neutrophil activation, by following physical cellular changes (size and shape—granulation) and by examining surface activation markers (increased CD11b surface expression). The neutrophil control stimulant fMLP was used to confirm the purified human neutrophils ability to activate. See FIG. 4.

Sequence Information

Total RNA was extracted from 656.35, 197.2 and 81.1 hybridoma cells, heavy and light variable domain cDNA sequence was then generated by reverse transcription and polymerase chain reaction (RT-PCR). The forward primer for RT-PCR was a mixture of degenerate primers specific for murine immunoglobulin gene leader-sequences and the reverse primer was specific for the antibody constant regions, in this case isotype IgG2a/κ. Primers were designed according to the strategy described by Jones and Bendig (Bio/Technology 9:88, 1991). RT-PCR was carried out in duplicate for both V-region sequences to enable subsequent verification of the correct V-region sequences. The V-region products generated by the RT-PCR were cloned (Invitrogen TA Cloning Kit) and sequence data obtained. This process was not successful for 81.1 light variable domain. Thus, the amino acid sequence shown below (Seq ID NO: 12) was therefore generated by protein sequencing the light chain isolated on a SDS-polyacrylamide gel run under reducing conditions.

Complementarity Determining Regions (CDRs) are underlined.

Polynucleotide sequences for heavy and light variable regions (SEQ ID NO: 1 and 3, respectively) for 656.35

```
                                              SEQ ID NO: 1
CAGGTCCAGTTGCAGCAGTCTGGAGCTGAACTGGTAAGGCCTGGGACTTC

AGTGACGATATCCTGTAAGGCTTCTGGCTACACCTTCACTAACTACTGGAT

AGTTTGGGTCAAACAGAGGCCTGGACATGGACTTGAGTGGATTGGAGATC

TTTACTCTGGAGGTGGTTATACTTTCTACAGTGAAAATTTCAAGGGGAAG

GCCACACTGACTGCAGACACATCCTCCAGCACTGCCTACATGCACCTCAT

TAGCCTGACATCTGAGGACTCTGCTGTCTATTTCTGTGCAAGATCGGGTTA
```

```
                                              -continued
CGACAGAACCTGGTTTGCTCACTGGGGCCAAGGGTCTCTGGTCACTGTCT

CTGCA

SEQ ID NO: 3
GACATCAAGATGACCCAGTCTCCATCCTCCATGTCTGCATCGCTGGGAGA

GAGAGTCACTATCACTTGTCAGGCGAGTCAGGACATTGAAAGCTATTTAA

GCTGGTATCAGCAGAAACCATGGAAATCTCCTAAGACCCTGATCTATTAC

GCTACAAGGTTGGCAGATGGGGTCCCATCAAGATTCAGTGGCAGTGGATC

TGGTCAAGATTATTCTCTAACCATCAGCAGCCTGGAGTCTGACGATACAG

CAACTTATTACTGTCTACAACATGGTGAGAGCCCTCCCACGTTCGGTGCTG

GGACCAAGCTGGAGCTGAAACGG
```

Polypeptide sequences for heavy and light variable regions (SEQ ID NO: 2 and 4, respectively) for 656.35

```
                                              SEQ ID NO: 2
QVQLQQSGAELVRPGTSVTISCKASGYTFT NYWIV WVKQRPGHGLEWIG

DLYSGGGYTFYSENFKG KATLTADTSSSTAYMHLISLTSEDSAVYFCAR

SGYDRTWFAH WGQGSLVTVSA

SEQ ID NO: 4
DIKMTQSPSSMSASLGERVTITC QASQDIESYLS WYQQKPWKSPKTLIY

YATRLAD GVPSRFSGSGSGQDYSLTISSLESDDTATYYC LQHGESPPT F

GAGTKLELKR
```

Polypeptide sequences for heavy chain CDRs (SEQ ID NO: 13, 14, 15, respectively) for 656.35

```
    NYWIV                    SEQ ID NO: 13

DLYSGGGYTFYSENFKG        SEQ ID NO: 14

SGYDRTWFAH               SEQ ID NO: 15
```

Polypeptide sequences for light chain CDRs (SEQ ID NO: 16, 17, 18) for 656.35

```
    QASQDIESYLS              SEQ ID NO: 16

YATRLAD                  SEQ ID NO: 17

LQHGESPPT                SEQ ID NO: 18
```

Polynucleotide sequences for heavy chain CDRs (SEQ ID NO: 31, 32, 33) for 656.35

SEQ ID NO: 31
AACTACTGGATAGTT

SEQ ID NO: 32
GATCTTTACTCTGGAGGTGGTTATACTTTCTACAGTGAAAATTTCAAGG
GG

SEQ ID NO: 33
TCGGGTTACGACAGAACCTGGTTTGCTCAC

Polynucleotide sequences for light chain CDRs (SEQ ID NO:34, 35, 36) for 656.35

SEQ ID NO: 34
CAGGCGAGTCAGGACATTGAAAGCTATTTAAGC

SEQ ID NO: 35
TACGCTACAAGGTTGGCAGAT

SEQ ID NO: 36
CTACAACATGGTGAGAGCCCTCCCACG

Polynucleotide sequences for heavy and light variable regions (SEQ ID NO: 5 and 7, respectively) for 197.2

SEQ ID NO: 5
GAGTTCCAGCTGCAGCAGTCTGGACCTGAGCTGGTGAAGCCTGGCGCTT
CAGTGAAGATATCCTGCAAGGCTTCTGGTTACTCATTCACTGACTACAA
CATGAACTGGGTGAAGCAGAGCAATGGAAAGAGCCTTGAGTGGATTGGA
GTAATTAATCCTAAGTATGGTACTACTAGTTACAATCAGAAGTTCAAGG
GCAAGGCCACGTTGACTGTAGACCAATCCTCCAACACAGCCTACATGCA
GCTCAGCAGCCTGACATCTGAGGACTCTGCAGTCTATCACTGTGCAAGA
GGAATGGGACTCCTCTTTGGTATGGACTACTGGGGCCAAGGAACCTCTG
TCACCGTCTCCTCA

SEQ ID NO: 7
GACATTGTGATGACACAGTCTCCATCCTCCCTGAGTGTGTCAGCAGGAG
AGAAGGTCACTATGAGCTGCAAGTCCAGTCAGAGTCTGTTAAACAGTGG
AAATCARAAGAACTACTTGGCCTGGTACCAGCAGAAACCAGGGCAGCCT
CCTAAACTGTTGATCTACGGGCATCCACTAGGAAATCTGGGGTCCCTG
ATCGCTTCACAGGCAGTGGATCTGGAACCGATTTCACTCTTACCATCAG
CAGTGTGCAGGCTGAAGACCTGGCAGTTTATTACTGTCAGAATGATCAT
AGTTTTCCGTGCACGTTCGGAGGGGGGACCAAGCTGGAAATAAAACGG

Polypeptide sequences for heavy and light variable regions (SEQ ID NO: 6 and 8, respectively) for 197.2

SEQ ID NO: 6
EFQLQQSGPELVKPGASVKISCKASGYSFT<u>DYNMN</u>WVKQSNGKSLEWIG
<u>VINPKYGTTSYNQKFKG</u>KATLTVDQSSNTAYMQLSSLTSEDSAVYHCAR
<u>GMGLLFGMDY</u>WGQGTSVTVSS

SEQ ID NO: 8
DIVMTQSPSSLSVSAGEKVTMSC<u>KSSQSLLNSGNQKNYLA</u>WYQQKPGQP
PKLLIY<u>GASTRKS</u>GVPDRFTGSGSGTDFTLTISSVQAEDLAVYYC<u>QNDH
SFPCT</u>FGGGTKLEIKR

Polypeptide sequences for heavy chain CDRs (SEQ ID NO: 19, 20, 21, respectively) for 197.2

DYNMN               SEQ ID NO: 19

VINPKYGTTSYNQKFKG   SEQ ID NO: 20

GMGLLFGMDY          SEQ ID NO: 21

Polypeptide sequences for light chain CDRs (SEQ ID NO: 22, 23, 24) for 197.2

KSSQSLLNSGNQKNYLA   SEQ ID NO: 22

GASTRKS             SEQ ID NO: 23

QNDHSFPCT           SEQ ID NO: 24

Polynucleotide sequences for heavy chain CDRs (SEQ ID NO: 37, 38, 39) for 197.2

SEQ ID NO: 37
GACTACAACATGAAC

SEQ ID NO: 38
GTAATTAATCCTAAGTATGGTACTACTAGTTACAATCAGAAGTTCAAGG
GC

SEQ ID NO: 39
GGAATGGGACTCCTCTTTGGTATGGACTAC

Polynucleotide sequences for light chain CDRs (SEQ ID NO:40, 41, 42) for 197.2

SEQ ID NO: 40
AAGTCCAGTCAGAGTCTGTTAAACAGTGGAAATCAAAAGAACTACTTGG
CC

SEQ ID NO: 41
GGGGCATCCACTAGGAAATCT

SEQ ID NO: 42
CAGAATGATCATAGTTTTCCGTGCACG

Polynucleotide sequence for heavy variable region (SEQ ID NO: 9) for 81.1

SEQ ID NO: 9
GAGGTCCAGCTGCAGCAGTCTGGACCTGAACTGGAGAAGCCTGGCGCTT
CAGTGAAGATATCCTGCAAGGCTTCTGGTTACTCTTTCACTGTCTACGG
CATGAACTGGGTGAGACAGAGCAATGGAAAGAGCCTTGAATGGATTGGA
AATTTTGATCCTTACTTTAGTGTCACTTCCTACAACCAGAAGTTCCAGG
ACAAGGCCACATTGACTGTAGACAAATCCTCCAGCACAGCCTACATGCA
GCTCAAGAACCTCACATCTGAAGACTCTGCAGTCTATTTCTGTGCAAGA
GGGAGCTGGGAAACCATTTTTGCTTACTGGGGCCAAGGGACTCTGGTCA
CTGTCTCTGCA

Polypeptide sequence for heavy variable region (SEQ ID NO: 10) for 81.1

```
                                          SEQ ID NO: 10
EVQLQQSGPELEKPGASVKISCKASGYSFTVYGMNWVRQSNGKSLEWIG

NFDPYFSVTSYNQKFQDKATLTVDKSSSTAYMQLKNLTSEDSAVYFCAR

GSWETIFAYWGQGTLVTVSA
```

Polypeptide sequences for heavy chain CDRs (SEQ ID NO: 25, 26, 27, respectively) for 81.1

```
    VYGMN              SEQ ID NO: 25
    NFDPYFSVTSYNQKFQD  SEQ ID NO: 26
    GSWETIFAY          SEQ ID NO: 27
```

Polynucleotide sequences for heavy chain CDRs (SEQ ID NO: 43, 44, 45) for 81.1

```
                                          SEQ ID NO: 43
GTCTACGGCATGAAC

SEQ ID NO: 44
AATTTTGATCCTTACTTTAGTGTCACTTCCTACAACCAGAAGTTCCAGG
AC

SEQ ID NO: 45
GGGAGCTGGGAAACCATTTTTGCTTAC
```

Polypeptide sequence for light variable region (SEQ ID NO: 12) for 81.1

```
QAVVTQESALTTSPGETVTLTCRSSTGAVTTSNYANWVQEKPDHLFTGL

IGGTNNRAPGVPARFSGSLIGDKAALTITGAQTEDEAIYFCALWYSNHV

FGGGTKLTVLQPK
```

Polypeptide sequences for light chain CDRs (SEQ ID NO: 28, 29, and 30, respectively) for 81.1

```
    RSSTGAVTTSNYAN    SEQ ID NO: 28
    GTNNRAP           SEQ ID NO: 29
    ALWYSNHV          SEQ ID NO: 30
```

A chimera* polynucleotide sequence (variable heavy region+codon optimised IgG1) SEQ ID NO: 55

```
CAGGTCCAGTTGCAGCAGTCTGGAGCTGAACTGGTAAGGCCTGGGACTTC

AGTGACGATATCCTGTAAGGCTTCTGGCTACACCTTCACTAACTACTGGA

TAGTTTGGGTCAAACAGAGGCCTGGACATGGACTTGAGTGGATTGGAGAT

CTTTACTCTGGAGGTGGTTATACTTTCTACAGTGAAAATTTCAAGGGGAA

GGCCACACTGACTGCAGACACATCCTCCAGCACTGCCTACATGCACCTCA

TTAGCCTGACATCTGAGGACTCTGCTGTCTATTTCTGTGCAAGATCGGGT

TACGACAGAACCTGGTTTGCTCACTGGGGCCAAGGGTCACTAGTGACCGT

GTCCAGCGCCAGCACCAAGGGCCCCAGCGTGTTCCCCCTGGCCCCCAGCA

GCAAGAGCACCAGCGGCGGCACAGCCGCCCTGGGCTGCCTGGTGAAGGAC
```

TACTTCCCCGAACCGGTGACCGTGTCCTGGAACAGCGGAGCCCTGACCAG

CGGCGTGCACACCTTCCCCGCCGTGCTGCAGAGCAGCGGCCTGTACAGCC

TGAGCAGCGTGGTGACCGTGCCCAGCAGCAGCCTGGGCACCCAGACCTAC

ATCTGTAACGTGAACCACAAGCCCAGCAACACCAAGGTGGACAAGAAGGT

GGAGCCCAAGAGCTGTGACAAGACCCACACCTGCCCCCCCTGCCCTGCCC

CCGAGCTGCTGGGAGGCCCCAGCGTGTTCCTGTTCCCCCCCAAGCCTAAG

GACACCCTGATGATCAGCAGAACCCCCGAGGTGACCTGTGTGGTGGTGGA

TGTGAGCCACGAGGACCCTGAGGTGAAGTTCAACTGGTACGTGGACGGCG

TGGAGGTGCACAATGCCAAGACCAAGCCCAGGGAGGAGCAGTACAACAGC

ACCTACCGGGTGGTGTCCGTGCTGACCGTGCTGCACCAGGATTGGCTGAA

CGGCAAGGAGTACAAGTGTAAGGTGTCCAACAAGGCCCTGCCTGCCCCTA

TCGAGAAAACCATCAGCAAGGCCAAGGGCCAGCCCAGAGAGCCCCAGGTG

TACACCCTGCCCCCTAGCAGAGATGAGCTGACCAAGAACCAGGTGTCCCT

GACCTGCCTGGTGAAGGGCTTCTACCCCAGCGACATCGCCGTGGAGTGGG

AGAGCAACGGCCAGCCCGAGAACAACTACAAGACCACCCCCCCTGTGCTG

GACAGCGATGGCAGCTTCTTCCTGTACAGCAAGCTGACCGTGGACAAGAG

CAGATGGCAGCAGGGCAACGTGTTCAGCTGCTCCGTGATGCACGAGGCCC

TGCACAATCACTACACCCAGAAGAGCCTGAGCCTGTCCCCTGGCAAG chimera* polypeptide sequence (variable heavy region+codon optimised IgG1) SEQ ID NO: 56

```
QVQLQQSGAELVRPGTSVTISCKASGYTFTNYWIVWVKQRPGHGLEWIGD

LYSGGGYTFYSENFKGKATLTADTSSSTAYMHLISLTSEDSAVYFCARSG

YDRTWFAHWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

A chimera* polynucleotide sequence (variable light region+codon optimised human cK) SEQ ID NO: 57

```
GACATCAAGATGACCCAGTCTCCATCCTCCATGTCTGCATCGCTGGGAGA

GAGAGTCACTATCACTTGTCAGGCGAGTCAGGACATTGAAAGCTATTTAA

GCTGGTATCAGCAGAAACCATGGAAATCTCCTAAGACCCTGATCTATTAC

GCTACAAGGTTGGCAGATGGGGTCCCATCAAGATTCAGTGGCAGTGGATC

TGGTCAAGATTATTCTCTAACCATCAGCAGCCTGGAGTCTGACGATACAG

CAACTTATTACTGTCTACAACATGGTGAGAGCCCTCCCACGTTCGGTGCT

GGGACCAAGCTGGAGCTGAAACGTACGGTGGCCGCCCCCAGCGTGTTCAT

CTTCCCCCCCAGCGATGAGCAGCTGAAGAGCGGCACCGCCAGCGTGGTGT
```

```
GTCTGCTGAACAACTTCTACCCCCGGGAGGCCAAGGTGCAGTGGAAGGTG
GACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGG
CCGACTACGAGAAGCACAAGGTGTACGCCTGTGAGGTGACCCACCAGGGC
CTGTCCAGCCCCGTGACCAAGAGCTTCAACCGGGGCGAGTGC
```

Chimera* polypeptide sequence (variable light region+ codon optimised human cK) SEQ ID NO: 58

```
DIKMTQSPSSMSASLGERVTITCQASQDIESYLSWYQQKPWKSPKTLIYY
ATRLADGVPSRFSGSGSGQDYSLTISSLESDDTATYYCLQHGESPPTFGA
GTKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
```

Chimera* refers to chimeric antibody made from murine 656.35 antibody

H0 DNA Sequence of Mature Heavy Chain SEQ ID NO: 11

```
CAGGTGCAGCTCGTGCAGAGCGGCGCCGAAGTGAAGAAGCCCGGGGCCAG
CGTGAAGGTGAGCTGCAAGGCCAGCGGCTACACCTTCACCAACTACTGGA
TCGTGTGGGTCAGGCAGGCCCCCGGCCAGGGACTGGAGTGGATGGGCGAC
CTGTATAGCGGCGGCGGCTACACCTTCTACAGCGAGAACTTCAAGGGCAG
GGTGACCATGACCAGGGACACCAGCACCAGCACCGTGTACATGGAGCTGA
GCAGCCTGAGGAGCGAGGACACCGCCGTGTACTACTGCGCCAGGAGCGGC
TACGACAGGACTTGGTTTGCTCACTGGGGCCAGGGCACACTAGTGACCGT
GTCCAGCGCCAGCACCAAGGGCCCCAGCGTGTTCCCCCTGGCCCCCAGCA
GCAAGAGCACCAGCGGCGGCACAGCCGCCCTGGGCTGCCTGGTGAAGGAC
TACTTCCCCGAACCGGTGACCGTGTCCTGGAACAGCGGAGCCCTGACCAG
CGGCGTGCACACCTTCCCCGCCGTGCTGCAGAGCAGCGGCCTGTACAGCC
TGAGCAGCGTGGTGACCGTGCCCAGCAGCAGCCTGGGCACCCAGACCTAC
ATCTGTAACGTGAACCACAAGCCCAGCAACACCAAGGTGGACAAGAAGGT
GGAGCCCAAGAGCTGTGACAAGACCCACACCTGCCCCCCCTGCCCTGCCC
CCGAGCTGCTGGGAGGCCCCAGCGTGTTCCTGTTCCCCCCCAAGCCTAAG
GACACCCTGATGATCAGCAGAACCCCCGAGGTGACCTGTGTGGTGGTGGA
TGTGAGCCACGAGGACCCTGAGGTGAAGTTCAACTGGTACGTGGACGGCG
TGGAGGTGCACAATGCCAAGACCAAGCCCAGGGAGGAGCAGTACAACAGC
ACCTACCGGGTGGTGTCCGTGCTGACCGTGCTGCACCAGGATTGGCTGAA
CGGCAAGGAGTACAAGTGTAAGGTGTCCAACAAGGCCCTGCCTGCCCCTA
TCGAGAAAACCATCAGCAAGGCCAAGGGCCAGCCCAGAGAGCCCCAGGTG
TACACCCTGCCCCCTAGCAGAGATGAGCTGACCAAGAACCAGGTGTCCCT
GACCTGCCTGGTGAAGGGCTTCTACCCCAGCGACATCGCCGTGGAGTGGG
AGAGCAACGGCCAGCCCGAGAACAACTACAAGACCACCCCCCCTGTGCTG
GACAGCGATGGCAGCTTCTTCCTGTACAGCAAGCTGACCGTGGACAAGAG
CAGATGGCAGCAGGGCAACGTGTTCAGCTGCTCCGTGATGCACGAGGCCC
TGCACAATCACTACACCCAGAAGAGCCTGAGCCTGTCCCTGGCAAG
```

H0 Protein Sequence of Mature Heavy Chain SEQ ID NO: 46

```
QVQLVQSGAEVKKPGASVKVSCKASGYTFTNYWIVWVRQAPGQGLEWMGD
LYSGGGYTFYSENFKGRVTMTRDTSTSTVYMELSSLRSEDTAVYYCARSG
YDRTWFAHWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK
```

L7 DNA Sequence of Mature Light Chain SEQ ID NO: 47

```
GATATCCAGATGACCCAGAGCCCTAGCTCCCTCAGCGCATCAGTCGGCGA
CAGAGTGACAATCACCTGCCAGGCATCCCAGGACATCGAGTCTTACCTGA
GCTGGTACCAGCAGAAGCCCGGAAAGGCCCCAAAGCTCCTGATCTACTAC
GCCACTCGGCTGGCAgacGGCGTGCCTAGCAGGTTCTCCGGCTCAGGGTC
TGGGACAGACTTCACCCTGACCATCAGCTCACTGCAGCCCGAGGATTTCG
CCACCTACTACTGTCTGCAGCACGGAGAGAGCCCCCCAACCTTTGGCCAG
GGAACCAAGCTGGAGATCaagCGTACGGTGGCCGCCCCCAGCGTGTTCAT
CTTCCCCCCCAGCGATGAGCAGCTGAAGAGCGGCACCGCCAGCGTGGTGT
GTCTGCTGAACAACTTCTACCCCCGGGAGGCCAAGGTGCAGTGGAAGGTG
GACAATGCCCTGCAGAGCGGCAACAGCCAGGAGAGCGTGACCGAGCAGGA
CAGCAAGGACTCCACCTACAGCCTGAGCAGCACCCTGACCCTGAGCAAGG
CCGACTACGAGAAGCACAAGGTGTACGCCTGTGAGGTGACCCACCAGGGC
CTGTCCAGCCCCGTGACCAAGAGCTTCAACCGGGGCGAGTGC
```

L7 Protein Sequence of Mature Light Chain SEQ ID NO: 48

```
DIQMTQSPSSLSASVGDRVTITCQASQDIESYLSWYQQKPGKAPKLLIYY
ATRLADGVPSRFSGSGSGTDFTLTISSLQPEDFATYYCLQHGESPPTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
```

L8 DNA Sequence of Mature Light Chain SEQ ID NO: 59

```
GATATCCAGATGACCCAGAGCCCTAGCTCCCTCAGCGCATCAGTCGGCGA
CAGAGTGACAATCACCTGCCAGGCATCCCAGGACATCGAGTCTTACCTGA
GCTGGTACCAGCAGAAGCCCGGAAAGGCCCCAAAGCTCCTGATCTACTAC
GCCACTCGGCTGGCAgacGGCGTGCCTAGCAGGTTCTCCGGCTCAGGGTC
TGGGACAGACTTCACCttcACCATCAGCTCACTGCAGCCCGAGGATatcG
```

CCACCTACTACTGTCTGCAGCACGGAGAGAGCCCCCCAACCTTTGGCCAG

GGAACCAAGCTGGAGATCaagCGTACGGTGGCCGCCCCCAGCGTGTTCAT

CTTCCCCCCCAGCGATGAGCAGCTGAAGAGCGGCACCGCCAGCGTGGTGT

GTCTGCTGAACAACTTCTACCCCGGGAGGCCAAGGTGCAGTGGAAGGTG

GACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGG

CCGACTACGAGAAGCACAAGGTGTACGCCTGTGAGGTGACCCACCAGGGC

CTGTCCAGCCCCGTGACCAAGAGCTTCAACCGGGGCGAGTGC

L8 protein sequence of mature light chain SEQ ID NO: 60

DIQMTQSPSSLSASVGDRVTITCQASQDIESYLSWYQQKPGKAPKLLIYY
ATRLADGVPSRFSGSGSGTDFTFTISSLQPEDIATYYCLQHGESPPTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

L10 DNA Sequence of Mature Light Chain SEQ ID NO: 61

GATATCCAGATGACCCAGAGCCCTAGCTCCCTCAGCGCATCAGTCGGCGA

CAGAGTGACAATCACCTGCCAGGCATCCCAGGACATCGAGTCTTACCTGA

GCTGGTACCAGCAGAAGCCCGGAAAGGCCCCAAAGCTCCTGATCTACTAC

GCCACTCGGCTGGCAgacGGCGTGCCTAGCAGGTTCTCCGGCTCAGGGTC

TGGGcagGACtacACCCTGACCATCAGCTCACTGCAGCCCGAGGATTTCG

CCACCTACTACTGTCTGCAGCACGGAGAGAGCCCCCCAACCTTTGGCCAG

GGAACCAAGCTGGAGATCAAGCGTACGGTGGCCGCCCCCAGCGTGTTCAT

CTTCCCCCCCAGCGATGAGCAGCTGAAGAGCGGCACCGCCAGCGTGGTGT

GTCTGCTGAACAACTTCTACCCCGGGAGGCCAAGGTGCAGTGGAAGGTG

GACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGG

CCGACTACGAGAAGCACAAGGTGTACGCCTGTGAGGTGACCCACCAGGGC

CTGTCCAGCCCCGTGACCAAGAGCTTCAACCGGGGCGAGTGC

L10 Protein Sequence of Mature Light Chain SEQ ID NO: 62

DIQMTQSPSSLSASVGDRVTITCQASQDIESYLSWYQQKPGKAPKLLIYY
ATRLADGVPSRFSGSGSGQDYTLTISSLQPEDFATYYCLQHGESPPTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

M0 DNA Sequence of Mature Light Chain SEQ ID NO: 63

GAGATCGTGCTGACCCAGTCTCCCGCCACCCTGTCACTGTCTCCCGGCGA

AAGGGCAACCCTGAGCTGCCAGGCCAGCCAGGACATCGAGAGCTACCTGA

GCTGGTACCAGCAGAAGCCCGGCCAGGCCCCAGGCTGCTGATCTACTAC

GCCACCAGGCTGGCCGACGGCATTCCCGCCAGGTTCAGCGGAAGCGGCAG

CGGCACCGACTTCACTCTGACCATCAGCAGCCTGGAGCCCGAGGACTTCG

CCGTGTACTACTGCCTGCAGCACGGCGAGAGCCCTCCCACCTTCGGCCAG

GGCACCAAGCTCGAGATCAAGCGTACGGTGGCCGCCCCCAGCGTGTTCAT

CTTCCCCCCCAGCGATGAGCAGCTGAAGAGCGGCACCGCCAGCGTGGTGT

GTCTGCTGAACAACTTCTACCCCGGGAGGCCAAGGTGCAGTGGAAGGTG

GACAATGCCCTGCAGAGCGGCAACAGCCAGGAGAGCGTGACCGAGCAGGA

CAGCAAGGACTCCACCTACAGCCTGAGCAGCACCCTGACCCTGAGCAAGG

CCGACTACGAGAAGCACAAGGTGTACGCCTGTGAGGTGACCCACCAGGGC

CTGTCCAGCCCCGTGACCAAGAGCTTCAACCGGGGCGAGTGC

M0 Protein Sequence of Mature Light Chain SEQ ID NO: 64

EIVLTQSPATLSLSPGERATLSCQASQDIESYLSWYQQKPGQAPRLLIYY
ATRLADGIPARFSGSGSGTDFTLTISSLEPEDFAVYYCLQHGESPPTFGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

We claim:

1. A method of treating inflammatory bowel disease (IBD) or psoriasis in a patient comprising administering to the patient an effective treatment amount of an antibody comprising heavy and light chain variable regions which comprise the CDR amino acid sequences of SEQ ID NOs: 13, 14, and 15; and SEQ ID NOs: 16, 17, and 18, respectively.

2. The method of treating IBD or psoriasis of claim 1 in which the antibody has heavy and light chains comprising the amino acid sequences of SEQ ID NO:46, and SEQ ID NO: 48, 60, 62, or 64, respectively.

3. The method of treating IBD or psoriasis of claim 1 in which the antibody has heavy and light chains comprising amino acid sequences of SEQ ID NO:46 and SEQ ID NO: 62, respectively.

4. The method of treating IBD or psoriasis of claim 1 in which the antibody is Humanized.

* * * * *

SEQUENCE LISTING

<160> NUMBER OF SEQ ID NOS: 64

<210> SEQ ID NO 1
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 1
caggtccagt tgcagcagtc tggagctgaa ctggtaaggc ctgggacttc agtgacgata     60
tcctgtaagg cttctggcta caccttcact aactactgga tagtttgggt caaacagagg    120

```
cctggacatg gacttgagtg gattggagat ctttactctg gaggtggtta tactttctac    180
agtgaaaatt tcaaggggaa ggccacactg actgcagaca catcctccag cactgcctac    240
atgcacctca ttagcctgac atctgaggac tctgctgtct atttctgtgc aagatcgggt    300
tacgacagaa cctggtttgc tcactggggc caagggtctc tggtcactgt ctctgca      357
```

<210> SEQ ID NO 2
<211> LENGTH: 119
<212> TYPE: PRT
<213> ORGANISM: Artificial Sequence
<220> FEATURE:
<223> OTHER INFORMATION: Amino acid sequence identified using molecular
   biology techniques.

<400> SEQUENCE: 2

```
Gln Val Gln Leu Gln Gln Ser Gly Ala Glu Leu Val Arg Pro Gly Thr
1               5                   10                  15

Ser Val Thr Ile Ser Cys Lys Ala Ser Gly Tyr Thr Phe Thr Asn Tyr
            20                  25                  30

Trp Ile Val Trp Val Lys Gln Arg Pro Gly His Gly Leu Glu Trp Ile
        35                  40                  45

Gly Asp Leu Tyr Ser Gly Gly Tyr Thr Phe Tyr Ser Glu Asn Phe
    50                  55                  60

Lys Gly Lys Ala Thr Leu Thr Ala Asp Thr Ser Ser Ser Thr Ala Tyr
65                  70                  75                  80

Met His Leu Ile Ser Leu Thr Ser Glu Asp Ser Ala Val Tyr Phe Cys
                85                  90                  95

Ala Arg Ser Gly Tyr Asp Arg Thr Trp Phe Ala His Trp Gly Gln Gly
            100                 105                 110

Ser Leu Val Thr Val Ser Ala
        115
```

<210> SEQ ID NO 3
<211> LENGTH: 324
<212> TYPE: DNA
<213> ORGANISM: Artificial Sequence
<220> FEATURE:
<223> OTHER INFORMATION: Nucleic acid sequence identified using
   molecular biology techniques.

<400> SEQUENCE: 3

```
gacatcaaga tgacccagtc tccatcctcc atgtctgcat cgctgggaga gagagtcact    60
atcacttgtc aggcgagtca ggacattgaa agctatttaa gctggtatca gcagaaacca    120
tggaaatctc ctaagaccct gatctattac gctacaaggt tggcagatgg ggtcccatca    180
agattcagtg gcagtggatc tggtcaagat tattctctaa ccatcagcag cctggagtct    240
gacgatacag caacttatta ctgtctacaa catggtgaga gccctcccac gttcggtgct    300
gggaccaagc tggagctgaa acgg                                           324
```

<210> SEQ ID NO 4
<211> LENGTH: 108
<212> TYPE: PRT
<213> ORGANISM: Artificial Sequence
<220> FEATURE:
<223> OTHER INFORMATION: Amino acid sequence identified using molecular
   biology techniques.

<400> SEQUENCE: 4

```
Asp Ile Lys Met Thr Gln Ser Pro Ser Ser Met Ser Ala Ser Leu Gly
1               5                   10                  15
```

Glu Arg Val Thr Ile Thr Cys Gln Ala Ser Gln Asp Ile Glu Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Arg Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Pro
                85                  90                  95

Thr Phe Gly Ala Gly Thr Lys Leu Glu Leu Lys Arg
            100                 105

<210> SEQ ID NO 5
<211> LENGTH: 357
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 5
gagttccagc tgcagcagtc tggacctgag ctggtgaagc ctggcgcttc agtgaagata      60
tcctgcaagg cttctggtta ctcattcact gactacaaca tgaactgggt gaagcagagc     120
aatggaaaga gccttgagtg gattggagta attaatccta gtatggtac tactagttac      180 aatcagaagt tcaagggcaa ggccacgttg actgtagacc aatcctccaa cacagcctac     240
atgcagctca gcagcctgac atctgaggac tctgcagtct atcactgtgc aagaggaatg     300
ggactcctct ttggtatgga ctactggggc caaggaacct ctgtcaccgt ctcctca        357

<210> SEQ ID NO 6
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Val Ile Asn Pro Lys Tyr Gly Thr Thr Ser Tyr Asn Gln Lys Phe
    50                  55                  60

Lys Gly Lys Ala Thr Leu Thr Val Asp Gln Ser Ser Asn Thr Ala Tyr
65                  70                  75                  80

Met Gln Leu Ser Ser Leu Thr Ser Glu Asp Ser Ala Val Tyr His Cys
                85                  90                  95

Ala Arg Gly Met Gly Leu Leu Phe Gly Met Asp Tyr Trp Gly Gln Gly
            100                 105                 110

Thr Ser Val Thr Val Ser Ser
        115

<210> SEQ ID NO 7

```
<211> LENGTH: 342
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 7
gacattgtga tgacacagtc tccatcctcc ctgagtgtgt cagcaggaga gaaggtcact      60
atgagctgca agtccagtca gagtctgtta aacagtggaa atcaraagaa ctacttggcc    120
tggtaccagc agaaaccagg gcagcctcct aaactgttga tctacggggc atccactagg    180
aaatctgggg tccctgatcg cttcacaggc agtggatctg gaaccgattt cactcttacc    240
atcagcagtg tgcaggctga agacctggca gtttattact gtcagaatga tcatagtttt    300
ccgtgcacgt tcggagggggg gaccaagctg gaaataaaac gg                      342

<210> SEQ ID NO 8
<211> LENGTH: 114
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

Asp Ile Val Met Thr Gln Ser Pro Ser Ser Leu Ser Val Ser Ala Gly
 1               5                  10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Phe Pro Cys Thr Phe Gly Gly Gly Thr Lys Leu Glu Ile
            100                 105                 110

Lys Arg

<210> SEQ ID NO 9
<211> LENGTH: 354
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 9
gaggtccagc tgcagcagtc tggacctgaa ctggagaagc ctggcgcttc agtgaagata     60
tcctgcaagg cttctggtta ctctttcact gtctacggca tgaactgggt gagacagagc    120
aatggaaaga gccttgaatg gattggaaat tttgatcctt actttagtgt cacttcctac    180
aaccagaagt tccaggacaa ggccacattg actgtagaca atcctccag cacagcctac    240 atgcagctca agaacctcac atctgaagac tctgcagtct atttctgtgc aagagggagc    300
tgggaaacca ttttgcttta ctggggccaa gggactctgg tcactgtctc tgca          354
```

```
<210> SEQ ID NO 10
<211> LENGTH: 118
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Glu Val Gln Leu Gln Gln Ser Gly Pro Glu Leu Glu Lys Pro Gly Ala
 1               5                  10                  15

Ser Val Lys Ile Ser Cys Lys Ala Ser Gly Tyr Ser Phe Thr Val Tyr
            20                  25                  30

Gly Met Asn Trp Val Arg Gln Ser Asn Gly Lys Ser Leu Glu Trp Ile
        35                  40                  45

Gly Asn Phe Asp Pro Tyr Phe Ser Val Thr Ser Tyr Asn Gln Lys Phe
    50                  55                  60

Gln Asp Lys Ala Thr Leu Thr Val Asp Lys Ser Ser Thr Ala Tyr
65                  70                  75                  80

Met Gln Leu Lys Asn Leu Thr Ser Glu Asp Ser Ala Val Tyr Phe Cys
                85                  90                  95

Ala Arg Gly Ser Trp Glu Thr Ile Phe Ala Tyr Trp Gly Gln Gly Thr
            100                 105                 110

Leu Val Thr Val Ser Ala
        115

<210> SEQ ID NO 11
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 11
caggtgcagc tcgtgcagag cggcgccgaa gtgaagaagc ccggggccag cgtgaaggtg      60
agctgcaagg ccagcggcta caccttcacc aactactgga tcgtgtgggt caggcaggcc    120
cccggccagg gactggagtg gatgggcgac ctgtatagcg gcggcggcta caccttctac    180
agcgagaact tcaagggcag ggtgaccatg accagggaca ccagcaccag caccgtgtac    240
atggagctga gcagcctgag gagcgaggac accgccgtgt actactgcgc caggagcggc    300
tacgacagga cttggtttgc tcactggggc cagggcacac tagtgaccgt gtccagcgcc    360
agcaccaagg gcccagcgt gttccccctg gcccccagca gcaagagcac cagcggcggc    420
acagccgccc tgggctgcct ggtgaaggac tacttccccg aaccggtgac cgtgtcctgg    480
aacagcggag ccctgaccag cggcgtgcac accttccccg ccgtgctgca gagcagcggc    540
ctgtacagcc tgagcagcgt ggtgaccgtg ccagcagca gcctgggcac ccagacctac    600
atctgtaacg tgaaccacaa gcccagcaac accaaggtgg acaagaaggt ggagcccaag    660
agctgtgaca gacccacac ctgcccccc tgccctgccc ccgagctgct gggaggcccc    720
agcgtgttcc tgttcccccc caagcctaag gacaccctga tgatcagcag aaccccgag    780 gtgacctgtg tggtggtgga tgtgagccac gaggaccctg aggtgaagtt caactggtac    840
gtggacggcg tggaggtgca caatgccaag accaagccca gggaggagca gtacaacagc    900
acctaccggg tggtgtccgt gctgaccgtg ctgcaccagg attggctgaa cggcaaggag    960
tacaagtgta aggtgtccaa caaggccctg cctgccccta tcgagaaaac catcagcaag    1020
```

```
gccaagggcc agcccagaga gccccaggtg tacaccctgc cccctagcag agatgagctg    1080
accaagaacc aggtgtccct gacctgcctg gtgaagggct tctacccag cgacatcgcc    1140 gtggagtggg agagcaacgg ccagcccgag aacaactaca agaccacccc ccctgtgctg    1200
gacagcgatg gcagcttctt cctgtacagc aagctgaccg tggacaagag cagatggcag    1260
cagggcaacg tgttcagctg ctccgtgatg cacgaggccc tgcacaatca ctacacccag    1320
aagagcctga gcctgtcccc tggcaag                                        1347
```

<210> SEQ ID NO 12
<211> LENGTH: 111
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 12

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Val Phe Gly Gly Gly Thr Lys Leu Thr Val Leu Gln Pro Lys
            100                 105                 110
```

<210> SEQ ID NO 13
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 13

```
Asn Tyr Trp Ile Val
1               5
```

<210> SEQ ID NO 14
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 14

```
Asp Leu Tyr Ser Gly Gly Gly Tyr Thr Phe Tyr Ser Glu Asn Phe Lys
1               5                   10                  15

Gly
```

<210> SEQ ID NO 15
<211> LENGTH: 10
<212> TYPE: PRT
<213> ORGANISM: Artificial Sequence

```
<220> FEATURE:
<223> OTHER INFORMATION: Amino acid sequence identified using molecular
      biology techniques.

<400> SEQUENCE: 15

Ser Gly Tyr Asp Arg Thr Trp Phe Ala His
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 16

Gln Ala Ser Gln Asp Ile Glu Ser Tyr Leu Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 17

Tyr Ala Thr Arg Leu Ala Asp
1               5

<210> SEQ ID NO 18
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 18

Leu Gln His Gly Glu Ser Pro Pro Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 19

Asp Tyr Asn Met Asn
1               5

<210> SEQ ID NO 20
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 20

Val Ile Asn Pro Lys Tyr Gly Thr Thr Ser Tyr Asn Gln Lys Phe Lys
1               5                   10                  15
```

Gly

<210> SEQ ID NO 21
<211> LENGTH: 10
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 21

Gly Met Gly Leu Leu Phe Gly Met Asp Tyr
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 22

Lys Ser Ser Gln Ser Leu Leu Asn Ser Gly Asn Gln Lys Asn Tyr Leu
1               5                   10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 23

Gly Ala Ser Thr Arg Lys Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 24

Gln Asn Asp His Ser Phe Pro Cys Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 25

Val Tyr Gly Met Asn
1               5

<210> SEQ ID NO 26
<211> LENGTH: 17
<212> TYPE: PRT
<213> ORGANISM: Artificial Sequence

```
<220> FEATURE:
<223> OTHER INFORMATION: Amino acid sequence identified using molecular
      biology techniques.

<400> SEQUENCE: 26

Asn Phe Asp Pro Tyr Phe Ser Val Thr Ser Tyr Asn Gln Lys Phe Gln
1               5                   10                  15

Asp

<210> SEQ ID NO 27
<211> LENGTH: 9
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 27

Gly Ser Trp Glu Thr Ile Phe Ala Tyr
1               5

<210> SEQ ID NO 28
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 28

Arg Ser Ser Thr Gly Ala Val Thr Thr Ser Asn Tyr Ala Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 29

Gly Thr Asn Asn Arg Ala Pro
1               5

<210> SEQ ID NO 30
<211> LENGTH: 8
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 30

Ala Leu Trp Tyr Ser Asn His Val
1               5

<210> SEQ ID NO 31
<211> LENGTH: 15
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 31
aactactgga tagtt                                                15
```

```
<210> SEQ ID NO 32
<211> LENGTH: 51
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 32
gatctttact ctggaggtgg ttatactttc tacagtgaaa atttcaaggg g            51

<210> SEQ ID NO 33
<211> LENGTH: 30
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 33
tcgggttacg acagaacctg gtttgctcac                                    30

<210> SEQ ID NO 34
<211> LENGTH: 33
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 34
caggcgagtc aggacattga aagctattta agc                                33

<210> SEQ ID NO 35
<211> LENGTH: 21
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 35
tacgctacaa ggttggcaga t                                             21

<210> SEQ ID NO 36
<211> LENGTH: 27
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 36
ctacaacatg gtgagagccc tcccacg                                       27

<210> SEQ ID NO 37
<211> LENGTH: 15
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 37
gactacaaca tgaac                                                    15
```

```
<210> SEQ ID NO 38
<211> LENGTH: 51
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 38
gtaattaatc ctaagtatgg tactactagt tacaatcaga agttcaaggg c          51

<210> SEQ ID NO 39
<211> LENGTH: 30
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 39
ggaatgggac tcctctttgg tatggactac                                   30

<210> SEQ ID NO 40
<211> LENGTH: 51
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 40
aagtccagtc agagtctgtt aaacagtgga aatcaaaaga actacttggc c          51

<210> SEQ ID NO 41
<211> LENGTH: 21
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 41
ggggcatcca ctaggaaatc t                                            21

<210> SEQ ID NO 42
<211> LENGTH: 27
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 42
cagaatgatc atagttttcc gtgcacg                                      27

<210> SEQ ID NO 43
<211> LENGTH: 15
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 43
gtctacggca tgaac                                                   15
```

-continued

```
<210> SEQ ID NO 44
<211> LENGTH: 51
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 44
aattttgatc cttactttag tgtcacttcc tacaaccaga agttccagga c          51

<210> SEQ ID NO 45
<211> LENGTH: 27
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 45
gggagctggg aaaccatttt tgcttac                                     27

<210> SEQ ID NO 46
<211> LENGTH: 449
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 46

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Trp Ile Val Trp Val Arg Gln Ala Pro Gly Gln Gly Leu Glu Trp Met
        35                  40                  45

Gly Asp Leu Tyr Ser Gly Gly Tyr Thr Phe Tyr Ser Glu Asn Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Asp Arg Thr Trp Phe Ala His Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

225               230                235                240
Ser Val Phe Leu Phe Pro Pro Lys Pro Lys Asp Thr Leu Met Ile Ser
                245                250                255

Arg Thr Pro Glu Val Thr Cys Val Val Val Asp Val Ser His Glu Asp
            260                265                270

Pro Glu Val Lys Phe Asn Trp Tyr Val Asp Gly Val Glu Val His Asn
        275                280                285

Ala Lys Thr Lys Pro Arg Glu Glu Gln Tyr Asn Ser Thr Tyr Arg Val
290                295                300

Val Ser Val Leu Thr Val Leu His Gln Asp Trp Leu Asn Gly Lys Glu
305                310                315                320

Tyr Lys Cys Lys Val Ser Asn Lys Ala Leu Pro Ala Pro Ile Glu Lys
                325                330                335

Thr Ile Ser Lys Ala Lys Gly Gln Pro Arg Glu Pro Gln Val Tyr Thr
            340                345                350

Leu Pro Pro Ser Arg Asp Glu Leu Thr Lys Asn Gln Val Ser Leu Thr
        355                360                365

Cys Leu Val Lys Gly Phe Tyr Pro Ser Asp Ile Ala Val Glu Trp Glu
    370                375                380

Ser Asn Gly Gln Pro Glu Asn Asn Tyr Lys Thr Thr Pro Pro Val Leu
385                390                395                400

Asp Ser Asp Gly Ser Phe Phe Leu Tyr Ser Lys Leu Thr Val Asp Lys
                405                410                415

Ser Arg Trp Gln Gln Gly Asn Val Phe Ser Cys Ser Val Met His Glu
            420                425                430

Ala Leu His Asn His Tyr Thr Gln Lys Ser Leu Ser Leu Ser Pro Gly
        435                440                445

Lys

<210> SEQ ID NO 47
<211> LENGTH: 642
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 47
gatatccaga tgacccagag ccctagctcc ctcagcgcat cagtcggcga cagagtgaca      60
atcacctgcc aggcatccca ggacatcgag tcttacctga ctggtaccag cagaagccc     120 ggaaaggccc caaagctcct gatctactac gccactcggc tggcagacgg cgtgcctagc    180
aggttctccg gctcagggtc tgggacagac ttcaccctga ccatcagctc actgcagccc    240
gaggatttcg ccacctacta ctgtctgcag cacggagaga gccccccaac ctttggccag    300
ggaaccaagc tggagatcaa gcgtacggtg gccgccccca gcgtgttcat cttcccccc     360 agcgatgagc agctgaagag cggcaccgcc agcgtggtgt gtctgctgaa caacttctac    420
ccccgggagg ccaaggtgca gtggaaggtg gacaatgccc tgcagagcgg caacagccag    480
gagagcgtga ccgagcagga cagcaaggac tccacctaca gcctgagcag caccctgacc    540
ctgagcaagg ccgactacga aaagcacaag gtgtacgcct gtgaggtgac ccaccagggc    600
ctgtccagcc ccgtgaccaa gagcttcaac cggggcgagt gc                       642

<210> SEQ ID NO 48
<211> LENGTH: 214

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 48

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Glu Ser Tyr
                 20                  25                  30

Leu Ser Trp Tyr Gln Gln Lys Pro Gly Lys Ala Pro Lys Leu Leu Ile
             35                  40                  45

Tyr Tyr Ala Thr Arg Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Gly Glu Ser Pro Pro
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 49
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 49

Leu Ala Thr Glu Leu Arg Ser Gln Ser Leu Gln Thr Leu Gln Gly
  1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 50

Ser Ala Lys Glu Leu Arg Ser Gln Ser Ile Lys Thr Tyr Ser Lys
  1               5                  10                  15
```

-continued

```
<210> SEQ ID NO 51
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 51

Leu Arg Glu Leu Arg Ser Val Ser Leu Gln Thr Thr Gln Gly
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 52

Ser Pro Gly Pro His Ser Ala Gln Thr Glu Val Ile Ala Thr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 53

Glu Ser Gly Pro His Ser Ala Asn Thr Glu Ile Ile Val Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 54

Lys Glu Leu Arg Cys Gln Cys Ile Lys Thr Tyr Ser Lys Pro
1               5                   10

<210> SEQ ID NO 55
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 55
caggtccagt tgcagcagtc tggagctgaa ctggtaaggc ctgggacttc agtgacgata      60
tcctgtaagg cttctggcta caccttcact aactactgga tagtttgggt caaacagagg     120
cctggacatg gacttgagtg gattggagat ctttactctg gaggtggtta tactttctac     180
agtgaaaatt tcaaggggaa ggccacactg actgcagaca catcctccag cactgcctac     240
atgcacctca ttagcctgac atctgaggac tctgctgtct atttctgtgc aagatcgggt     300
tacgacagaa cctggtttgc tcactggggc caagggtcac tagtgaccgt gtccagcgcc     360
agcaccaagg gcccagcgt gttccccctg gccccagca gcaagagcac cagcggcggc      420
```

-continued

```
acagccgccc tgggctgcct ggtgaaggac tacttccccg aaccggtgac cgtgtcctgg      480
aacagcggag ccctgaccag cggcgtgcac accttccccg ccgtgctgca gagcagcggc      540
ctgtacagcc tgagcagcgt ggtgaccgtg cccagcagca gcctgggcac ccagacctac      600
atctgtaacg tgaaccacaa gcccagcaac accaaggtgg acaagaaggt ggagcccaag      660
agctgtgaca gacccacac ctgccccccc tgccctgccc ccgagctgct gggaggcccc       720
agcgtgttcc tgttccccccc caagcctaag gacaccctga tgatcagcag aaccccgag     780 gtgacctgtg tggtggtgga tgtgagccac gaggaccctg aggtgaagtt caactggtac     840
gtggacggcg tggaggtgca caatgccaag accaagccca gggaggagca gtacaacagc     900
acctaccggg tggtgtccgt gctgaccgtg ctgcaccagg attggctgaa cggcaaggag     960
tacaagtgta aggtgtccaa caaggccctg cctgccccta tcgagaaaac catcagcaag     1020
gccaagggcc agcccagaga gccccaggtg tacaccctgc ccctagcag agatgagctg      1080 accaagaacc aggtgtccct gacctgcctg gtgaagggct tctacccag cgacatcgcc      1140 gtggagtggg agagcaacgg ccagcccgag aacaactaca agaccacccc ccctgtgctg     1200
gacagcgatg gcagcttctt cctgtacagc aagctgaccg tggacaagag cagatggcag     1260
cagggcaacg tgttcagctg ctccgtgatg cacgaggccc tgcacaatca ctacacccag     1320
aagagcctga gcctgtcccc tggcaag                                         1347
```

<210> SEQ ID NO 56
<211> LENGTH: 449
<212> TYPE: PRT
<213> ORGANISM: Artificial Sequence
<220> FEATURE:
<223> OTHER INFORMATION: Amino acid sequence identified using molecular biology techniques.

<400> SEQUENCE: 56

```
Gln Val Gln Leu Gln Gln Ser Gly Ala Glu Leu Val Arg Pro Gly Thr
 1               5                  10                  15

Ser Val Thr Ile Ser Cys Lys Ala Ser Gly Tyr Thr Phe Thr Asn Tyr
            20                  25                  30

Trp Ile Val Trp Val Lys Gln Arg Pro Gly His Gly Leu Glu Trp Ile
        35                  40                  45

Gly Asp Leu Tyr Ser Gly Gly Tyr Thr Phe Tyr Ser Glu Asn Phe
    50                  55                  60

Lys Gly Lys Ala Thr Leu Thr Ala Asp Thr Ser Ser Ser Thr Ala Tyr
65                  70                  75                  80

Met His Leu Ile Ser Leu Thr Ser Glu Asp Ser Ala Val Tyr Phe Cys
                85                  90                  95

Ala Arg Ser Gly Tyr Asp Arg Thr Trp Phe Ala His Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 57
<211> LENGTH: 642
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 57
gacatcaaga tgacccagtc tccatcctcc atgtctgcat cgctgggaga gagagtcact         60
atcacttgtc aggcgagtca ggacattgaa agctatttaa gctggtatca gcagaaacca        120
tggaaatctc ctaagaccct gatctattac gctacaaggt tggcagatgg ggtcccatca        180
agattcagtg gcagtggatc tggtcaagat tattctctaa ccatcagcag cctggagtct        240
gacgatacag caacttatta ctgtctacaa catggtgaga gcctcccac gttcggtgct         300 gggaccaagc tggagctgaa acgtacggtg gccgccccca gcgtgttcat cttcccccc         360 agcgatgagc agctgaagag cggcaccgcc agcgtggtgt gtctgctgaa caacttctac        420 cccgggagg ccaaggtgca gtggaaggtg acaatgccc tgcagagcgg caacagccag          480
gagagcgtga ccgagcagga cagcaaggac tccacctaca gcctgagcag caccctgacc        540

```
ctgagcaagg ccgactacga gaagcacaag gtgtacgcct gtgaggtgac ccaccagggc      600
ctgtccagcc ccgtgaccaa gagcttcaac cggggcgagt gc                        642
```

```
<210> SEQ ID NO 58
<211> LENGTH: 214
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 58
```

| | | | | | | | | | | | | | | |
|---|---|---|---|---|---|---|---|---|---|---|---|---|---|---|
| Asp | Ile | Lys | Met | Thr | Gln | Ser | Pro | Ser | Ser | Met | Ser | Ala | Ser | Leu | Gly |
| 1 | | | | 5 | | | | | 10 | | | | | 15 | |

Glu Arg Val Thr Ile Thr Cys Gln Ala Ser Gln Asp Ile Glu Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Arg Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Pro
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 59
<211> LENGTH: 642
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 59
gatatccaga tgacccagag ccctagctcc ctcagcgcat cagtcggcga cagagtgaca      60
atcacctgcc aggcatccca ggacatcgag tcttacctga ctggtacca gcagaagccc     120 ggaaaggccc caaagctcct gatctactac gccactcggc tggcagacgg cgtgcctagc     180
aggttctccg gctcagggtc tgggacagac ttcaccttca ccatcagctc actgcagccc     240
gaggatatcg ccacctacta ctgtctgcag cacggagaga gccccccaac ctttggccag     300
```

```
ggaaccaagc tgagatcaa gcgtacggtg gccgccccca gcgtgttcat cttcccccccc    360 agcgatgagc agctgaagag cggcaccgcc agcgtggtgt gtctgctgaa caacttctac    420 ccccggggagg ccaaggtgca gtggaaggtg acaatgccc tgcagagcgg caacagccag    480
gagagcgtga ccgagcagga cagcaaggac tccacctaca gcctgagcag cacctgacc    540 ctgagcaagg ccgactacga gaagcacaag gtgtacgcct gtgaggtgac ccaccagggc    600
ctgtccagcc ccgtgaccaa gagcttcaac cggggcgagt gc                      642
```

<210> SEQ ID NO 60
<211> LENGTH: 214
<212> TYPE: PRT
<213> ORGANISM: Artificial Sequence
<220> FEATURE:
<223> OTHER INFORMATION: Amino acid sequence identified using molecular biology techniques.

<400> SEQUENCE: 60

```
Asp Ile Gln Met Thr Gln Ser Pro Ser Ser Leu Ser Ala Ser Val Gly
 1               5                   10                  15

Asp Arg Val Thr Ile Thr Cys Gln Ala Ser Gln Asp Ile Glu Ser Tyr
            20                  25                  30

Leu Ser Trp Tyr Gln Gln Lys Pro Gly Lys Ala Pro Lys Leu Leu Ile
        35                  40                  45

Tyr Tyr Ala Thr Arg Leu Ala Asp Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln His Gly Glu Ser Pro Pro
             85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 61
<211> LENGTH: 642
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 61

```
gatatccaga tgacccagag ccctagctcc ctcagcgcat cagtcggcga cagagtgaca    60
atcacctgcc aggcatccca ggacatcgag tcttacctga ctggtacca gcagaagccc   120
```

```
ggaaaggccc caaagctcct gatctactac gccactcggc tggcagacgg cgtgcctagc      180
aggttctccg gctcagggtc tgggcaggac tacaccctga ccatcagctc actgcagccc      240
gaggatttcg ccacctacta ctgtctgcag cacggagaga gcccccccaac ctttggccag     300 ggaaccaagc tggagatcaa agcgtacggtg gccgccccca gcgtgttcat cttcccccc      360 agcgatgagc agctgaagag cggcaccgcc agcgtggtgt gtctgctgaa caacttctac      420 ccccggggagg ccaaggtgca gtggaaggtg gacaatgccc tgcagagcgg caacagccag    480
gagagcgtga ccgagcagga cagcaaggac tccacctaca gcctgagcag caccctgacc      540
ctgagcaagg ccgactacga aagcacaag gtgtacgcct gtgaggtgac ccaccagggc      600
ctgtccagcc ccgtgaccaa gagcttcaac cggggcgagt gc                        642
```

<210> SEQ ID NO 62
<211> LENGTH: 214
<212> TYPE: PRT
<213> ORGANISM: Artificial Sequence
<220> FEATURE:
<223> OTHER INFORMATION: Amino acid sequence identified using molecular biology techniques.

<400> SEQUENCE: 62

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Glu Ser Tyr
            20                  25                  30

Leu Ser Trp Tyr Gln Gln Lys Pro Gly Lys Ala Pro Lys Leu Leu Ile
        35                  40                  45

Tyr Tyr Ala Thr Arg Leu Ala Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 642
<212> TYPE: DNA
<213> ORGANISM: Artificial Sequence
<220> FEATURE:
<223> OTHER INFORMATION: Nucleic acid sequence identified using molecular biology techniques.

<400> SEQUENCE: 63

```
gagatcgtgc tgacccagtc tcccgccacc ctgtcactgt ctcccggcga aagggcaacc      60
ctgagctgcc aggccagcca ggacatcgag agctacctga gctggtacca gcagaagccc     120
ggccaggccc ccaggctgct gatctactac gccaccaggc tggccgacgg cattcccgcc     180
aggttcagcg gaagcggcag cggcaccgac ttcactctga ccatcagcag cctggagccc     240
gaggacttcg ccgtgtacta ctgcctgcag cacggcgaga gccctcccac cttcggccag     300
ggcaccaagc tcgagatcaa gcgtacggtg gccgccccca gcgtgttcat cttccccccc     360
agcgatgagc agctgaagag cggcaccgcc agcgtggtgt gtctgctgaa caacttctac     420
ccccggagg ccaaggtgca gtggaaggtg gacaatgccc tgcagagcgg caacagccag      480
gagagcgtga ccgagcagga cagcaaggac tccacctaca gcctgagcag caccctgacc     540
ctgagcaagg ccgactacga gaagcacaag gtgtacgcct gtgaggtgac ccaccagggc     600
ctgtccagcc ccgtgaccaa gagcttcaac cggggcgagt gc                        642
```

<210> SEQ ID NO 64
<211> LENGTH: 214
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 64

```
Glu Ile Val Leu Thr Gln Ser Pro Ala Thr Leu Ser Leu Ser Pro Gly
  1               5                  10                  15

Glu Arg Ala Thr Leu Ser Cys Gln Ala Ser Gln Asp Ile Glu Ser Tyr
             20                  25                  30

Leu Ser Trp Tyr Gln Gln Lys Pro Gly Gln Ala Pro Arg Leu Leu Ile
         35                  40                  45

Tyr Tyr Ala Thr Arg Leu Ala Asp Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Leu Gln His Gly Glu Ser Pro Pro
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```